(12) United States Patent
Mackenzie et al.

(10) Patent No.: US 10,065,920 B2
(45) Date of Patent: Sep. 4, 2018

(54) CRYSTALLINE SOLID FORMS OF THE ACETATE SALT OF (1S,3S,4R)-4-((3AS,4R,5S,7AS)-4-(AMINOMETHYL)-7A-METHYL-1-METHYLENEOCTAHYDRO-1H-INDEN-5-YL)-3-(HYDROXYMETHYL)-4-METHYLCYCLOHEXANOL

(71) Applicant: Aquinox Pharmaceuticals (Canada) Inc., Vancouver (CA)

(72) Inventors: Lloyd F. Mackenzie, North Vancouver (CA); Jeffery R. Raymond, Vancouver (CA); Curtis Harwig, Vancouver (CA); Ana Fernandez Casares, Amsterdam (NL)

(73) Assignee: Aquinox Pharmaceuticals (Canada) Inc., Vancouver (CA)

( * ) Notice: Subject to any disclaimer, the term of this patent is extended or adjusted under 35 U.S.C. 154(b) by 0 days.

(21) Appl. No.: 15/885,387

(22) Filed: Jan. 31, 2018

(65) Prior Publication Data

US 2018/0155273 A1    Jun. 7, 2018

Related U.S. Application Data

(62) Division of application No. 15/191,134, filed on Jun. 23, 2016.

(60) Provisional application No. 62/185,416, filed on Jun. 26, 2015.

(51) Int. Cl.
*C07C 215/42* (2006.01)

(52) U.S. Cl.
CPC ........ *C07C 215/42* (2013.01); *C07B 2200/13* (2013.01); *C07C 2601/14* (2017.05); *C07C 2602/08* (2017.05); *C07C 2602/24* (2017.05)

(58) Field of Classification Search
None
See application file for complete search history.

(56) References Cited

U.S. PATENT DOCUMENTS

| | | |
|---|---|---|
| 3,682,983 A | 8/1972 | Prezewowsky et al. |
| 3,869,467 A | 3/1975 | Guthrie et al. |
| 3,962,275 A | 6/1976 | Guthrie et al. |
| 5,686,621 A | 11/1997 | Clark et al. |
| 6,046,185 A | 4/2000 | Burgoyne et al. |
| 6,635,629 B2 | 10/2003 | Raymond et al. |
| 6,696,580 B2 | 2/2004 | Burgoyne et al. |
| 6,982,329 B2 | 1/2006 | Burgoyne et al. |
| 7,601,874 B2 | 10/2009 | Raymond et al. |
| 7,999,010 B2 | 8/2011 | Raymond et al. |

(Continued)

FOREIGN PATENT DOCUMENTS

| | | |
|---|---|---|
| DE | 1 084 718 | 7/1960 |
| GB | 1291644 | 10/1972 |

(Continued)

OTHER PUBLICATIONS

Ahmad and Khan, "The Baeyer—Villiger Oxidation of 5α-Cholestane-3,6-Dione,"*Acta Chim. Acad. Sci. Hung.* 106(2): 111-113, 1981.

(Continued)

*Primary Examiner* — Sudhakar Katakam
*Assistant Examiner* — Jennifer C Sawyer
(74) *Attorney, Agent, or Firm* — Seed IP Law Group LLP

(57) ABSTRACT

The present invention is generally directed to novel crystalline forms of the acetate salt of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol and processes for their preparation.

5 Claims, 16 Drawing Sheets

XRPD diffractogram of Compound 1 Form B

(56) References Cited

U.S. PATENT DOCUMENTS

| | | | |
|---|---|---|---|
| 8,084,503 B2 | 12/2011 | Raymond et al. | |
| 8,673,975 B2 | 3/2014 | Raymond et al. | |
| 9,000,050 B2 | 4/2015 | Wang et al. | |
| 9,765,085 B2 | 9/2017 | Mackenzie et al. | |
| 2001/0010293 A1 | 8/2001 | Ishida et al. | |
| 2010/0323990 A1 | 12/2010 | Andersen et al. | |
| 2011/0263539 A1 | 10/2011 | Andersen et al. | |
| 2012/0270901 A1* | 10/2012 | Raymond | C07C 35/21 |
| | | | 514/319 |
| 2014/0371252 A1 | 12/2014 | Raymond et al. | |
| 2016/0083387 A1 | 3/2016 | Mackenzie et al. | |
| 2016/0376222 A1 | 12/2016 | Mackenzie et al. | |
| 2017/0362250 A1 | 12/2017 | Mackenzie et al. | |
| 2018/0085460 A1 | 3/2018 | Mackenzie et al. | |
| 2018/0086691 A9 | 3/2018 | Harwig et al. | |

FOREIGN PATENT DOCUMENTS

| | | |
|---|---|---|
| JP | 1-290624 A | 11/1989 |
| JP | 5-221901 A | 8/1993 |
| JP | 5-221924 A | 8/1993 |
| WO | WO 93/13124 A1 | 7/1993 |
| WO | WO 94/14833 A2 | 7/1994 |
| WO | WO 95/01960 A1 | 1/1995 |
| WO | WO 96/11939 A1 | 4/1996 |
| WO | WO 03/033517 A1 | 4/2003 |
| WO | WO 2004/035601 A1 | 4/2004 |
| WO | WO 2004/092100 A1 | 10/2004 |
| WO | WO 2007/147251 A1 | 12/2007 |
| WO | WO 2007/147252 A1 | 12/2007 |
| WO | WO 2011/069118 A1 | 6/2011 |
| WO | WO 2014/143561 A1 | 9/2014 |
| WO | WO 2014/158654 A1 | 10/2014 |
| WO | WO 2016/210146 A1 | 12/2016 |
| WO | WO 2017/127753 A1 | 7/2017 |
| WO | WO 2018/058144 A1 | 3/2018 |

OTHER PUBLICATIONS

Altomare et al., "SIR97: a new tool for crystal structure determination and refinement," *J. Appl. Cryst. 32*: 115-119, 1999.
Barber et al., "PI3Kγ inhibition blocks glomerulonephritis and extends lifespan in a mouse model of systemic lupus," *Nature Medicine 11*(9): 933-935, Sep. 2005.
Buckingham et al., "6-Phenylazocholestane derivatives: Reassignment of the Structures of Products from Phenylhydrazine and Ozonised Cholesterol Derivatives," *J. Chem. Soc.(C)* 18: 1703-1706, 1967.
Camps et al., "Blockade of PI3Kγ suppresses joint inflammation and damage in mouse models of rheumatoid arthritis," *Nature Medicine 11*(9): 936-943, Sep. 2005.
Clinton et al., "Steroidal[3,2-c]pyrazoles. II. Androstanes, 19-Norandrostanes and their Unsaturated Analogs," *Journal of the American Chemical Society 83*: 1478-1491, Mar. 20, 1961.
Coggeshall et al., "How do inhibitory phosphatases work?," *Molecular Immunology 39*: 521-529, 2002.
Cookson et al., "Photochemical Rearrangement of α-Hydroxyketones to Lactones," *J. Chem. Soc.* (C): 2494-2500, 1968.
Damen et al., "The 145-kDa protein induced to associate with Shc by multiple cytokines is an inositol tetraphosphate and phosphatidylinositol 3,4,5-trisphosphate 5-phosphatase," *Proc. Natl. Acad. Sci. USA 93*: 1689-1693, Feb. 1996.
Dauben and Brookhart, "Stereocontrolled Synthesis of Steroidal Side Chains," *J. Am. Chem. Soc. 103*: 237-238, 1981.
Deane et al., "Phosphoinositide 3-Kinase: Diverse Roles in Immune Cell Activation," *Annu. Rev. Immunol. 22*: 563-598, 2004.
Fan et al., "A dual PI3 kinase/mTOR inhibitor reveals emergent efficacy in glioma," *Cancer Cell 9*: 341-349, May 2006.
Feuer et al., "The Reduction of Oximes, Oxime Ethers, and Oxime Esters with Diborane. A Novel Synthesis of Amines," *The Journal of Organic Chemistry 34*(6): 1817-1821, Jun. 1969.

Fukuda et al., "Alteration of phosphatidylinositol 3-kinase cascade in the multilobulated nuclear formation of adult T cell leukemia/lymphoma (ATLL)," *PNAS 102*(42): 15213-15218, Oct. 18, 2005.
Gallou et al., "Practical Synthesis of Unsymmetrical Ureas from Isopropenyl Carbamates," *J. Org. Chem 70*: 6960-6963, 2005.
Goclik et al., "Pelorol from the Tropical Marine Sponge *Dactylospongia elegans*," *J. Nat. Prod. 63*: 1150-1152, 2000.
Gumulka et al, "Oxidative Cleavage of the Double Bond of 7-Dehydrocholesterol Acetate Peroxide," *Polish Journal of Chemistry 57*(4/5/6): 403-411, 1983.
Habermacher et al., "Prostatitis/Chronic Pelvic Pain Syndrome," *Annu. Rev. Med. 57*: 195-206, 2006.
Halpern et al., "On the Nature of the Chemical Mediators Involved in Anaphylactic Reactions in Mice," *Brit. J. Pharmacol. 20*: 389-398, 1963.
Hara, "Azasteroid. IV. Synthesis of B-Azacholane Derivative," Chemical Abstracts Online, Accession No. 1959:17427, 1959. See also *Yakugaku Zasshi 78*(9): 1030-1033, Sep. 1958.
Hazen et al., "SHIP is required for a functional hematopoietic stem cell niche," *Blood 113*(13): 2924-2933, Mar. 26, 2009.
Helgason et al., "A Dual Role for Src Homology 2 Domain-containing Inositol-5-Phosphatase (SHIP) in Immunity: Aberrant Development and Enhanced Function of B Lymphocytes in SHIP$^{-/-}$ Mice," *J. Exp. Med. 191*(5): 781-794, Mar. 6, 2000
Helgason et al., "Targeted disruption of *SHIP* leads to hemopoietic perturbations, lung pathology, and a shortened life span," *Genes & Development 12*: 1610-1620, 1998.
Hennessy et al., "Exploiting the PI3K/AKT Pathway for Cancer Drug Discovery," *Nature Reviews\Drug Discovery 4*: 988-1004, Dec. 2005.
Ibers et al., "Dispersion corrections and crystal structure refinements," *Acta Cryst. 17*: 781-782, 1964.
Kalesnikoff et al., "The role of SHIP in cytokine-induced signaling," *Rev. Physiol. Biochem. Pharmacol. 149*: 87-103, 2003.
Kaspar and Witzel, "Steroid Binding to the Cytosolic Estrogen Receptor From Rat Uterus. Influence of the Orientation of Substituents in the 17-Position of the 8β-and 8α-Series," *J. steroid Biochem. 23*(3): 259-265, 1985 .
Krieger et al., "NIH Consensus Definition and Classification of Prostatitis," *JAMA 281*(3): 236-237, Jul. 21, 1999.
Kubinyi, (3D QSAR in Drug Design: Ligand-Protein Interactions and Molecular Similarity, vol. 2-3, Springer, 1998, 800 pages), pp. 243-244 provided.
Knight et al., "A Pharmacological Map of the PI3-K Family Defines a Role for p110α in Insulin Signaling," *Cell 125*: 733-747, May 19, 2006.
Kwak et al., "Sesquiterpene Quinols/Quinones from the Micronesian Sponge *Petrosaspongia metachromia*," *J. Nat. Prod. 63*: 1153-1156, 2000.
Leaker et al., "The effects of the novel SHIP1 activator AQX-1125 on allergen-induced responses in mild-to-moderate asthma," *Clinical & Experimental Allergy 44*: 1146-1153, 2014.
Lettré and Werner, "Polyols from steroids and steroid derivatives. IV. 7,8-Seco-derivatives of cholestanols," Chemical Abstracts Online, Accession No. 1967:46521, 1967. See Also *Justus Liebigs Annalen Der Chemie 697*: 217-221, 1966.
Lettré and Werner, "Mehrwertige Alkohole aus Sterinen and Sterinderivaten. IV. 7.8-seco-Dcrivate des Cholestanols,"*Justus Liebigs Annalen Der Chemie 697*: 217-221, 1966.
Ley et al., "Microencapsulation of Osmium Tetroxide in Polyurea," *Organic Letters 5*(2): 185-187, 2003.
Liang et al., "Quantification of change in phosphorylation of BCR-ABL kinase and its substrates in response to Imatinib treatment in human chronic myelogenous leukemia cells," *Proteomics 6*: 4554-4564, 2006.
Luo et al., "Mutation Analysis of SHIP Gene in Acute Leukemia," *Journal of Experimental Hematology 12*(4): 420-426, 2004.
Macrae et al., "*Mercury CSD 2.0*—new features for the visualization and investigation of crystal structures " *J. Appl. Cryst. 41*: 466-470, 2008.
Madaio et al., "Minor 5,6-Secosterols From the Marine Sponge *Hippospongia Communis*. Isolation and Synthesis of (7Z,22E,24R)-

(56) References Cited

OTHER PUBLICATIONS

24-Methyl-5,6-Secocholesta-7,22-Diene-3β,5β,6-Triol," *Journal of Natural Products* 53(3): 565-572, May-Jun. 1990.

Manson et al., "Steroidal Heterocycles. VII. Androstano[2,3-d]isoxazoles and Related Compounds," *J. Med. Chem.* 6(1): 1-9, Jan. 18, 1963.

Mincione and Bovicelli, Synthesis via Organoiron Complexes of 9-(4-Keto-1-Methylcyclohex-2-enyl)-8-Keto-des-AB-Ergost-22,23-ene; A Useful Chiral Intermediate in Steroid Synthesis, *Heterocycles* 23(7): 1607-1610, 1985.

Mirjafary et al., "Oxime ethers as versatile precursors in organic synthesis: a review," *RSC Adv.* 5: 79361-79384, 2015.

Nickel et al., "Category III Chronic Prostatitis/Chronic Pelvic Pain Syndrome: Insights from The National Institutes of Health Chronic Prostatitis Collaborative Research Network Studies," *Curr Urol. Rep.* 9(4): 320-327, 2008.

Nickel et al., "A Phase II Study of the Efficacy and Safety of the Novel Oral SHIP1 Activator AQX-1125 in Subjects with Moderate to Severe Interstitial Cystitis/Bladder Pain Syndrome," *The Journal of Urology* 196: 747-754, Sep. 2016.

Nicolaou et al., "An Expedient Procedure for the Oxidative Cleavage of Olefinic Bonds with PhI(OAc)$_2$, NMO, and Catalytic OSO$_4$," *Org. Lett.* 12(7): 1552-1555, Apr. 2, 2010.

Ong et al., "Small-molecule agonists of SHIP1 inhibit the phosphoinositide 3-kinase pathway in hematopoietic cells," *Blood* 110(6): 1942-1949, Sep. 15, 2007.

Ovary et al., "Passive Cutaneous Anaphylaxis in the Mouse," *J. Immunol.* 81: 355-357, 1958.

Radhakrishnan et al., "Development and characterization of a novel animal model of prostate inflammation-induced chronic pelvic pain," *Inflammopharmacology* 17: 23-28, 2009.

Reichstein and Meystre, "Über Bestandteile der Nebennierenrinde und verwandte Stoffe—Allo-pregnan-diol-(3, 17)-Derivate der 17(β)-Reihe. Weiterer Beweis für die Zugehörigkeit der Substanzen P und K zur 17(β)-Reihe,"*Helv. Chim. Acta* 22(III): 728-741, 1939.

Rodewald and Piotrowski, "Secosteroids. I. Synthesis of vic-Diols in B-Secocholestane Group," *Journal Prakt. Chem.* 330(5): 775-881, 1988.

Rodewald and Wielógorski, "Selective Esterification of Hydroxyl Groups in Methyl Ester of 3β,8α-Dihydroxy-7,8-Secocholestan-7-oic Acid," *Roczniki Chemii Ann. Soc. Chim. Polonorum* 51(4): 809-814, 1977.

Rohrschneider et al., "Structure, function, and biology of SHIP proteins," *Genes & Development* 14: 505-520, 2000.

Savitzky et al., "Smoothing and Differentiation of Data by Simplified Least Squares Procedures," *Analytical Chemistry* 36(8): 1627-1639, Jul. 1964.

Seto et al., "Epimerization at C-5 of brassinolide with sodium methoxide and the biological activity of 5-epi-brassinolide in the rice lamina inclination test," *J. Chem. Soc., Perkin Trans. 1*: 3355-3358, 1998.

Simon, "Using Isoform-Specific Inhibitors to Target Lipid Kinases," *Cell* 125: 647-649, May 19, 2006.

Sly et al., "SHIP, SHIP2, and PTEN activities are regulated in vivo by modulation of their protein levels: SHIP is up-regulated in macrophages and mast cells by lipopolysaccharide," *Experimental Hematology* 31: 1170-1181, 2003.

Sly et al., "LPS—Induced Upregulation of SHIP Is Essential for Endotoxin Tolerance," *Immunity* 21: 227-239, Aug. 2004.

Speckamp et al., "6-Thiasteroids A Novel Stereoselective Preparation of 6-Heterosteroids," *Tetrahedron Letters* 38: 3405-3408, 1974.

Stenton et al., "Characterization of AQX-1125, a small-molecule SHIP1 activator Part 1. Effects on inflammatory cell activation and chemotaxis in vitro and pharmacokinetic characterization in vivo," *British Journal of Pharmacology* 168: 1506-1518, 2013.

Suginome and Yamada, "Photoinduced Transformations. 77. A Four-Step Substitution of a Carbonyl Group of Steroidal Ketones by an Oxygen Atom. A New Method for the Synthesis of Cyclic Ethers," *Journal of Organic Chemistry* 50(14): 2489-2494, 1985.

Tu et al., "Painful urological syndromes: Overview of the diagnosis and treatment of painful bladder syndrome/interstitial cystitis and chronic non-bacterial prostatitis/chronic pelvic pain syndrome (CPPS)," *Doul. et Analq.* 20: 154-166, 2007.

Vanderwinden et al., "Differences in signaling pathways and expression level of the phosphoinositide phosphatase SHIP1 between two oncogenic mutants of the receptor tyrosine kinase KIT," *Cellular Signalling* 18: 661-669, 2006.

Vivanco et al., "The Phosphatidylinositol 3-Kinase-AKT Pathway in Human Cancer," *Nature Reviews: Cancer* 2: 489-501, Jul. 2002.

Vonakis et al., "Src homology 2 domain-containing inositol 5' phosphatase is negatively associated with histamine release to human recombinant histamine-releasing factor in human basophils," *J. Allergy Clin. Immunol.* 108: 822-831, 2001.

Vykhovanets et al., "Experimental rodent models of prostatitis: limitations and potential," *Prostate Cancr and Prostatic Diseases* 10: 15-29, 2007.

Wermuth, The Practice of Medicinal Chemistry, 2nd ed. (2003), 26 pages, Chapters 9-10 provided.

Westmijze et al., "Ag(I)-Assisted Hydrolysis of Mestranol Methanesulfonate Into Epimestranol," *Tetrahedron Letters* 21: 2665-2666, Apr. 15, 1980.

Winter et al., "Carrageenin-Induced Edema in Hind Paw of the Rat as an Assay for Antiinflammatory Drugs," *Proc. Soc. Exp. Biol. Med.* 111: 544-547, 1962.

Workman et al., "Drugging the PI3 kinome," *Nature Biotechnology* 24(7): 794-796, Jul. 2006.

Xing et al., "Gold(I)-Catalyzed Oxidative Cleavage of a C-C Double Bond in Water," *Organic Letters* 8(4): 693-696, 2006.

Yang et al., "Ruthenium-Catalyzed Oxidative Cleavage of Olefins to Aldehydes," *J. Org. Chem.* 66: 4814-4818, 2001.

Yang et al., "Synthesis of Pelorol and Analogues: Activators of the Inositol 5-Phosphatase SHIP," *Organic Letters* 7(6): 1073-1076, 2005.

Yong et al., "Synthesis of CD-ring modified 1α,25-dihydroxy vitamin D analogues: Five-membered D-ring analogues," *Bioorganic & Medicinal Chemistry Letters* 7(7): 923-928, 1997.

Beilstein Database, Beilstein Registry No. 3061562, 1968.
Beilstein Database, Beilstein Registry No. 3102039, 1967.
Chemical Abstracts Database, Accession No. 82:73301, 1974.
Chemical Abstracts Database, Accession No. 101:192278, 1983.
Chemical Abstracts Database, Accession No. 112:211000, Nov. 1989.
Chemical Abstracts Database, Accession No. 120:77523, Aug. 1993.
Chemical Abstracts Online, Accession No. 1959:17427, 1959, 2 pages.
Chemical Abstracts Online, Accession No. 1967:46521, 1966, 2 pages.
Chemical Abstracts Online, Accession No. 2013:381943, 2013, 2 pages.
International Preliminary Report on Patentability, dated Oct. 21, 2005, for International Application No. PCT/CA2004/000566, 8 pages.
International Preliminary Report on Patentability, dated Sep. 15, 2015, for International Application No. PCT/US2014/019125, 8 pages.
International Preliminary Report on Patentability, dated Sep. 15, 2015, for International Application No. PCT/US2014/019126, 11 pages.
International Search Report, dated Sep. 6, 2016, for PCTAN PCT/US2016/039040, 6 pages.
Written Opinion of the International Searching Authority, dated Sep. 6, 2016, for PCTAN PCT/US2016/039040, 9 pages.
International Search Report, dated Mar. 13, 2017, for PCTAN PCT/US2017/014446, 5 pages.
Written Opinion of the International Searching Authority, dated Mar. 13, 2017, for PCTAN PCT/US2017/014446, 7 pages.
International Search Report and Written Opinion, dated Dec. 11, 2017, for PCTAN PCT/US2017/053554, 14 pages.
U.S. Appl. No. 14/162,136, filed Jan. 23, 2014, Indene Derivatives as Pharmaceutical Agents.

(56) References Cited

OTHER PUBLICATIONS

U.S. Appl. No. 14/772,737, filed Sep. 3, 2015, SHIP1 Modulators and Methods Related Thereto.
U.S. Appl. No. 15/411,863, filed Jan. 20, 2017, Synthesis of a Substituted Indene Derivative.
U.S. Appl. No. 15/676,726, filed Aug. 14, 2017, SHIP1 Modulators and Methods Related Thereto.
U.S. Appl. No. 15/884,044, filed Jan. 30, 2018, SHIP 1 Modulators and Methods Related Thereto.

* cited by examiner

XRPD diffractogram of crystalline Compound 1 Form A

DSC thermogram of Compound 1 Form A

TGA thermogram of Compound 1 Form A

Molecular structure of Compound 1 Form A

Comparison of the simulated powder pattern based on the single crystal data (bottom) and the experimental X-ray diffractogram (top) prepared from Compound 1 Form A Packing arrangement and hydrogen bond scheme along the β-axis of Compound 1 based on the single crystal data.

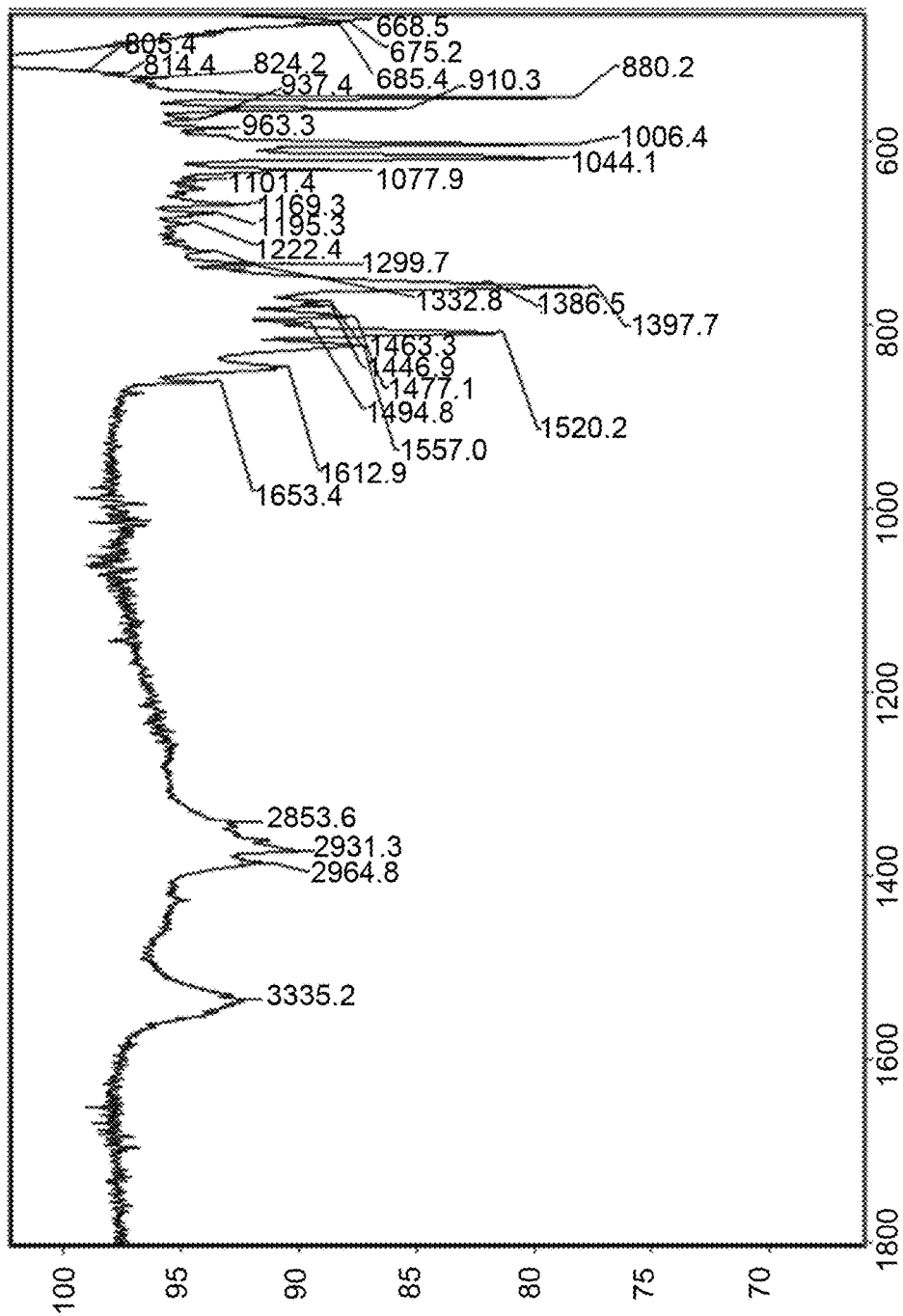

CRYSTALLINE SOLID FORMS OF THE ACETATE SALT OF (1S,3S,4R)-4-((3AS,4R,5S,7AS)-4-(AMINOMETHYL)-7A-METHYL-1-METHYLENEOCTAHYDRO-1H-INDEN-5-YL)-3-(HYDROXYMETHYL)-4-METHYLCYCLOHEXANOL

CROSS-REFERENCE TO RELATED APPLICATIONS

This application is a divisional application of U.S. patent application Ser. No. 15/191,134, filed on Jun. 23, 2016 (now allowed); which claims the benefit under 35 U.S.C. § 119(e) of U.S. Provisional Patent Application No. 62/185,416, filed on Jun. 26, 2015; the relevant disclosures of which are incorporated herein by reference in their entireties.

FIELD OF THE INVENTION

The present invention is generally directed to novel crystalline forms of the acetate salt of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol, processes for their preparation, and pharmaceutical compositions containing them.

BACKGROUND OF THE INVENTION

Dysregulated activation of the PI3K pathway contributes to inflammatory/immune disorders and cancer. Efforts have been made to develop modulators of PI3K as well as downstream kinases (Workman et al., Nat. Biotechnol 24, 794-796, 2006; Simon, Cell 125, 647-649, 2006; Hennessy et al., Nat Rev Drug Discov 4, 988-1004, 2005; Knight et al., Cell 125, 733-747, 2006; Ong et al., Blood (2007), Vol. 110, No. 6, pp 1942-1949). A number of promising new PI3K isoform specific inhibitors with minimal toxicities have recently been developed and used in mouse models of inflammatory disease (Camps et al., Nat Med 11, 936-943, 2005; Barber et al., Nat Med 11, 933-935, 2005) and glioma (Fan et al., Cancer Cell 9, 341-349, 2006). However, because of the dynamic interplay between phosphatases and kinases in regulating biological processes, inositol phosphatase activators represent a complementary, alternative approach to reduce $PIP_3$ levels. Of the phosphoinositol phosphatases that degrade $PIP_3$, SHIP1 is a particularly ideal target for development of therapeutics for treating immune and hemopoietic disorders because of its hematopietic-restricted expression (Hazen et al., Blood 113, 2924-2933, 2009; Rohrschneider et al., Genes Dev. 14, 505-520, 2000).

Small molecule SHIP1 modulators have been disclosed, including sesquiterpene compounds such as pelorol. Pelorol is a natural product isolated from the tropical marine sponge *Dactylospongia elegans* (Kwak et al., J Nat Prod 63, 1153-1156, 2000; Goclik et al., J Nat Prod 63, 1150-1152, 2000). Other reported SHIP1 modulators include the compounds set forth in PCT Published Patent Applications Nos. WO 2003/033517, WO 2004/035601, WO 2004/092100, WO 2007/147251, WO 2007/147252, WO 2011/069118, WO 2014/143561 and WO 2014/158654 and in U.S. Pat. Nos. 7,601,874 and 7,999,010.

While significant strides have been made in this field, there remains a need for effective small molecule SHIP1 modulators.

One such molecule is the acetate salt of (1S,3S,4R)-4-(3aS,4R,5S,7aS)-4-(aminomethyl)-7a-methyl-1-methyleneoctahydro-1H-inden-5-yl)-3-(hydroxymethyl)-4-methylcyclohexanol (referred to herein as Compound 1). Compound 1 is a compound with anti-inflammatory activity and is described in U.S. Pat. Nos. 7,601,874 and 7,999,010, the relevant disclosures of which are incorporated in full by reference in their entirety, particularly with respect to the preparation of Compound 1, pharmaceutical compositions comprising Compound 1 and methods of using Compound 1.

Compound 1 has the molecular formula, $C_{20}H_{36}NO_2^+ \cdot C_2H_3O_2^-$, a molecular weight of 381.5 g/mole and has the following structural formula:

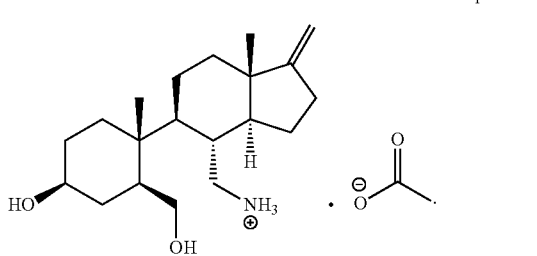

Compound 1

Compound 1 is useful in treating disorders and conditions that benefit from SHIP1 modulation, such as cancers, inflammatory disorders and conditions and immune disorders and conditions. Compound 1 is also useful in the preparation of a medicament for the treatment of such disorders and conditions.

SUMMARY OF THE INVENTION

The present invention is generally directed to novel crystalline forms of Compound 1, processes for their preparation, pharmaceutical compositions containing them and methods of using the novel crystalline forms and their compositions.

Accordingly, in one aspect, this invention is directed to a first novel crystalline form of Compound 1, referred to herein as Compound 1 Form A.

In another aspect, this invention is directed to a second novel crystalline form of Compound 1, referred to herein as Compound 1 Form B.

In another aspect, this invention is directed to compositions comprising a pharmaceutically acceptable excipient, carrier and/or diluent and Compound 1 Form A.

In another aspect, this invention is directed to compositions comprising a pharmaceutically acceptable excipient, carrier and/or diluent and Compound 1 Form B.

In another aspect, this invention is directed to a method for modulating SHIP1 activity in a mammal comprising administering an effective amount of Compound 1 Form A or an effective amount of a composition comprising Compound 1 Form A to the mammal in need thereof.

In another aspect, this invention is directed to a method for modulating SHIP1 activity in a mammal comprising administering an effective amount of Compound 1 Form B or an effective amount of a composition comprising Compound 1 Form B to the mammal in need thereof.

In another aspect, this invention is directed to a method for treating a disease, disorder or condition associated with SHIP1 activity in a mammal comprising administering an effective amount of Compound 1 Form A or an effective amount of a composition comprising Compound 1 Form A to the mammal in need thereof.

In another aspect, this invention is directed to a method for treating a disease, disorder or condition associated with SHIP1 activity in a mammal comprising administering an effective amount of Compound 1 Form B or an effective amount of a composition comprising Compound 1 Form B to the mammal in need thereof.

In another aspect, this invention is directed to methods for the preparation of Compound 1 Form A.

In another aspect, this invention is directed to methods for the preparation of Compound 1 Form B.

These aspects, and embodiments thereof, are described in more detail below. To this end, various references are set forth herein which describe in more detail certain background information, procedures, compounds and/or compositions, and are each hereby incorporated by reference in their entirety.

BRIEF DESCRIPTION OF THE FIGURES

FIG. 8A illustrates the full FT-IR spectrum of Compound 1 Form A.

DETAILED DESCRIPTION OF THE INVENTION

Figure 1:
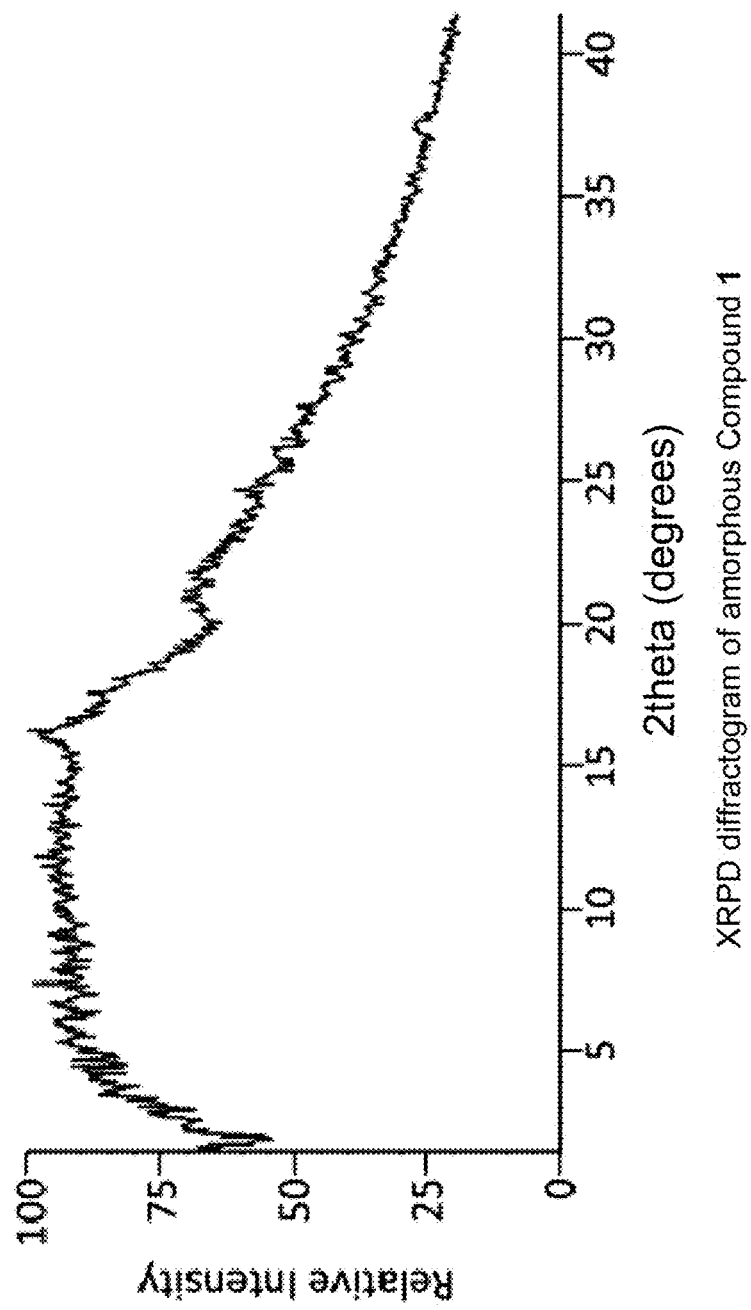
FIG. 1 illustrates the X-Ray Powder Diffraction pattern of amorphous Compound 1.

As mentioned above, the present invention is generally directed to novel crystalline forms of Compound 1, processes for their preparation, pharmaceutical compositions containing them and methods of using the novel crystalline forms.

In general, most pharmaceutical compounds, i.e., those compounds which are useful as pharmaceutical agents, are initially produced in amorphous forms which can be characterized by only short range ordering. These compounds may be challenging to develop, as the amorphous form is often unstable relative to a crystalline form and may convert under certain conditions to any crystalline form, not necessarily the most stable one. In an embodiment of the invention, molecules of Compound 1 in the crystalline form have both short and long range ordering and have different physical properties as compared to the amorphous form.

Solid state physical properties of a material affect the ease with which the material is handled during processing into a pharmaceutical product, such as a tablet or capsule formulation. The physical properties affect the types of excipients, for example, to be added to a formulation for a pharmaceutical compound. Furthermore, the solid state physical property of a pharmaceutical compound is important to its dissolution in aqueous and liquid milieus, including gastric juices, thereby having therapeutic consequences. The solid state form of a pharmaceutical compound may also affect its storage requirements. From a physicochemical perspective, the crystalline form of a pharmaceutical compound is the preferred form. Organization of the molecules in an ordered fashion to form a crystal lattice provides improved chemical stability, flowability, and other powder properties including reduced moisture sorption. All of these properties are of importance to the manufacturing, formulation, storage and overall manageability of a pharmaceutical drug product.

Thus, practical physical characteristics are influenced by the particular solid form of a substance. One solid form may give rise to different thermal behavior from that of the amorphous material or other solid forms. Thermal behavior is measured in the laboratory by such techniques as capillary melting point, thermo-gravimetric analysis (TGA) and differential scanning calorimetry (DSC) and can be used to distinguish some polymorphic solid forms from others. A particular polymorphic solid form may also give rise to distinct physical properties that may be detectable by X-ray powder diffraction (XRPD), solid state $^{13}$C-Nuclear Magnetic Resonance spectroscopy, and infrared or Raman spectrometry.

Compound 1 exists in an amorphous form, referred to herein as amorphous Compound 1. This invention is therefore directed to stable crystalline forms of Compound 1, i.e., Compound 1 Form A and Compound 1 Form B, whose properties can be influenced by controlling the conditions under which Compound 1 is obtained in solid form. The characteristics and properties of Compound 1 Form A and Compound 1 Form B are each described detail below.

Abbreviations

The following abbreviations may be used herein as needed:
DAD for diode array detector;
DSC for Differential scanning calorimetry;
FT-IR for Fourier transform Infrared Spectroscopy
FWHM for Full Width at Half Maximum;
HPLC for High Performance Liquid Chromatography;
m.p. for melting point;
PTFE for polytetrafluoroethylene;
rpm for revolutions per minute;
SDTA for Simultaneous differential thermal analysis;
TFA for trifluoroacetic acid;
TGA for Thermogravimetric analysis;
TGA/MS for Thermogravimetric analysis coupled with Mass Spectroscopy; and
XRPD for X-ray powder diffraction.

Compound 1 Form A

In one embodiment of the invention, Compound 1 Form A is provided, characterized by the selection of one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, or twenty-seven X-ray powder diffraction peaks selected from the group consisting of 6.0, 8.9, 10.7, 11.9, 13.3, 14.9, 15.8, 17.9, 18.4, 18.9, 19.9, 20.1, 20.3, 21.6, 23.6, 24.0, 24.5, 24.8, 25.3, 25.5, 25.8, 26.1, 26.9, 27.0, 27.2, 27.7, 27.9 degrees 2Θ±0.3 degrees 2Θ, more preferably ±0.2 degrees 2Θ, even more preferably ±0.1 degrees 2Θ, most preferably ±0.05 degrees 2Θ.

In another embodiment, Compound 1 Form A is characterized by the following set of XRPD peaks and, optionally, by the associated intensities listed in Table 1:

TABLE 1

XRPD PEAK TABLE FOR COMPOUND 1 FORM A

| | Embodiment | | | Preferred embodiment | | |
|---|---|---|---|---|---|---|
| Peak ID | Angle (2Θ) | d-Value | Intensity* | Angle (2Θ) | d-Value | Intensity* |
| 1 | 6.0 | 14.8 | L | 5.9719 | 14.7875 | L |
| 2 | 8.9 | 9.9 | H | 8.9297 | 9.8950 | H |
| 3 | 10.7 | 8.2 | M | 10.7454 | 8.2267 | M |
| 4 | 11.9 | 7.4 | M | 11.9490 | 7.4006 | M |
| 5 | 13.3 | 6.6 | M | 13.3350 | 6.6344 | M |
| 6 | 14.9 | 5.9 | L | 14.9310 | 5.9286 | L |
| 7 | 15.8 | 5.6 | H | 15.8040 | 5.6030 | H |
| 8 | 17.9 | 5.0 | M | 17.8991 | 4.9516 | M |
| 9 | 18.4 | 4.8 | L | 18.4005 | 4.8178 | L |
| 10 | 18.9 | 4.7 | L | 18.8893 | 4.6942 | L |
| 11 | 19.9 | 4.5 | M | 19.8539 | 4.4683 | M |
| 12 | 20.1 | 4.4 | M | 20.0844 | 4.4175 | M |
| 13 | 20.3 | 4.4 | H | 20.2699 | 4.3775 | H |
| 14 | 21.6 | 4.1 | L | 21.5792 | 4.1148 | L |
| 15 | 23.6 | 3.8 | L | 23.6037 | 3.7662 | L |
| 16 | 24.0 | 3.7 | L | 24.0130 | 3.7030 | L |
| 17 | 24.5 | 3.6 | L | 24.5354 | 3.6253 | L |
| 18 | 24.8 | 3.6 | L | 24.7525 | 3.5940 | L |
| 19 | 25.3 | 3.5 | L | 25.2688 | 3.5217 | L |
| 20 | 25.5 | 3.5 | L | 25.4612 | 3.4955 | L |
| 21 | 25.8 | 3.5 | L | 25.7788 | 3.4532 | L |
| 22 | 26.1 | 3.4 | L | 26.1404 | 3.4062 | L |
| 23 | 26.9 | 3.3 | L | 26.8526 | 3.3175 | L |
| 24 | 27.0 | 3.3 | L | 26.9880 | 3.3011 | L |
| 25 | 27.2 | 3.3 | L | 27.1630 | 3.2803 | L |
| 26 | 27.7 | 3.2 | L | 27.6680 | 3.2215 | L |
| 27 | 27.9 | 3.2 | L | 27.8793 | 3.1976 | L |

*For normalized intensity values: L = 3-25, M = 25-60, H = 60-100.

Figure 2:
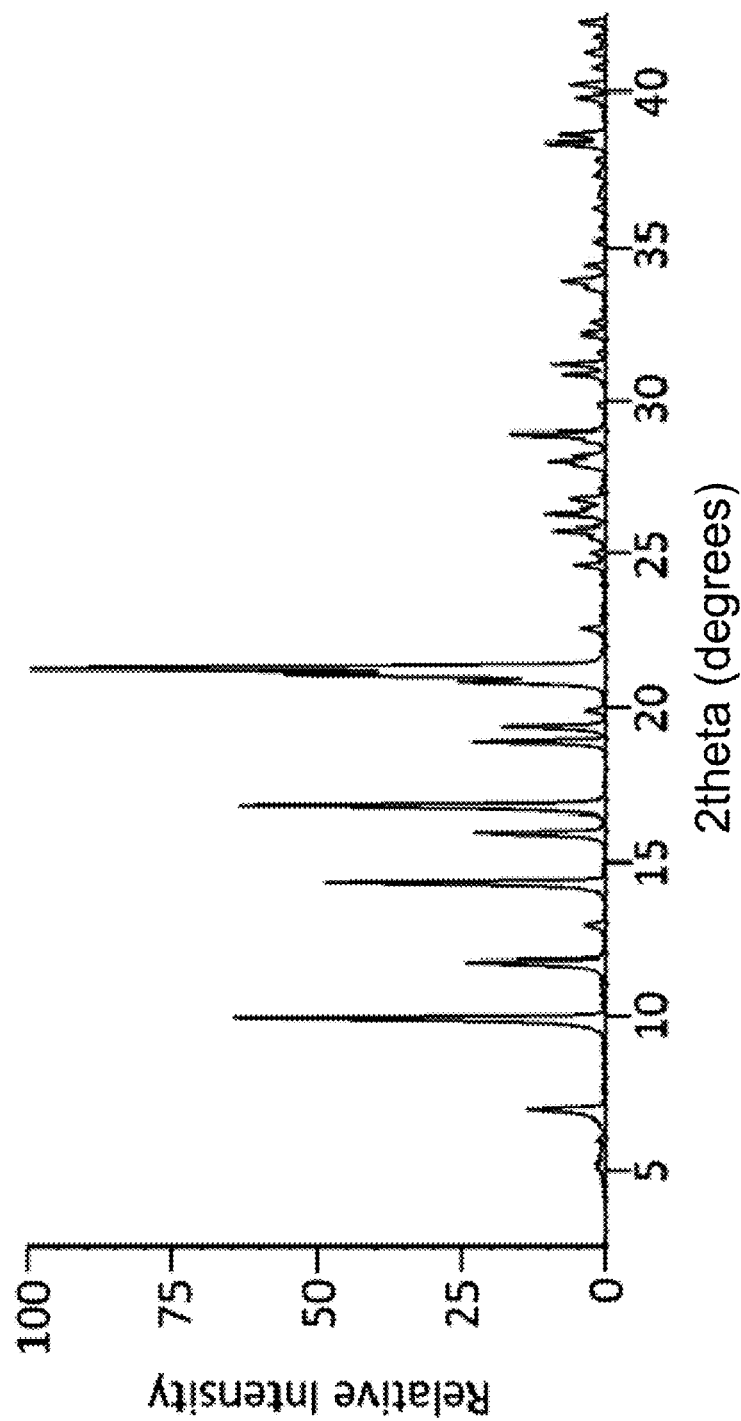
FIG. 2 illustrates the X-Ray Powder Diffraction pattern of Compound 1 Form A.

In another embodiment, Compound 1 Form A is characterized by an XRPD substantially according to FIG. 2.

In a preferred embodiment, Compound 1 Form A is characterized by an XRPD containing at least one of the following peaks: 5.96, 8.92, 10.74, 13.33 and 15.80 degrees 2Θ±0.3 degrees 2Θ, more preferably ±0.2 degrees 2Θ, even more preferably ±0.1 degrees 2Θ, most preferably ±0.05 degrees 2Θ. In a more preferred embodiment, Compound 1 Form A is characterized by an XRPD containing at least two of the following peaks: 5.96, 8.92, 10.74, 13.33 and 15.80 degrees 2Θ±0.3 degrees 2Θ, more preferably ±0.2 degrees 2Θ, even more preferably ±0.1 degrees 2Θ, most preferably ±0.05 degrees 2Θ.

Figure 3:
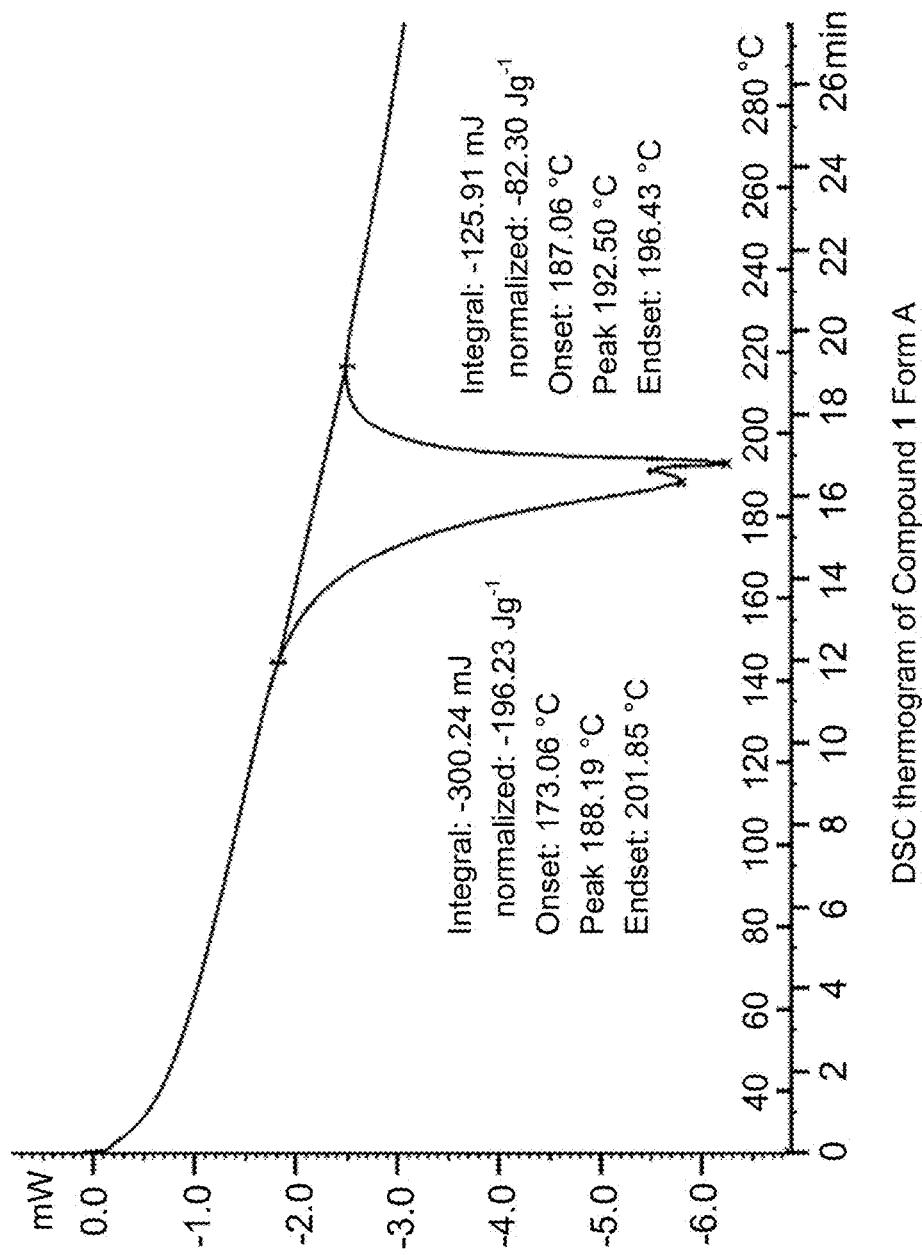
FIG. 3 illustrates the DSC thermogram of Compound 1 Form A.

In another embodiment, Compound 1 Form A is characterized by a DSC thermogram substantially according to FIG. 3.

Figure 4:
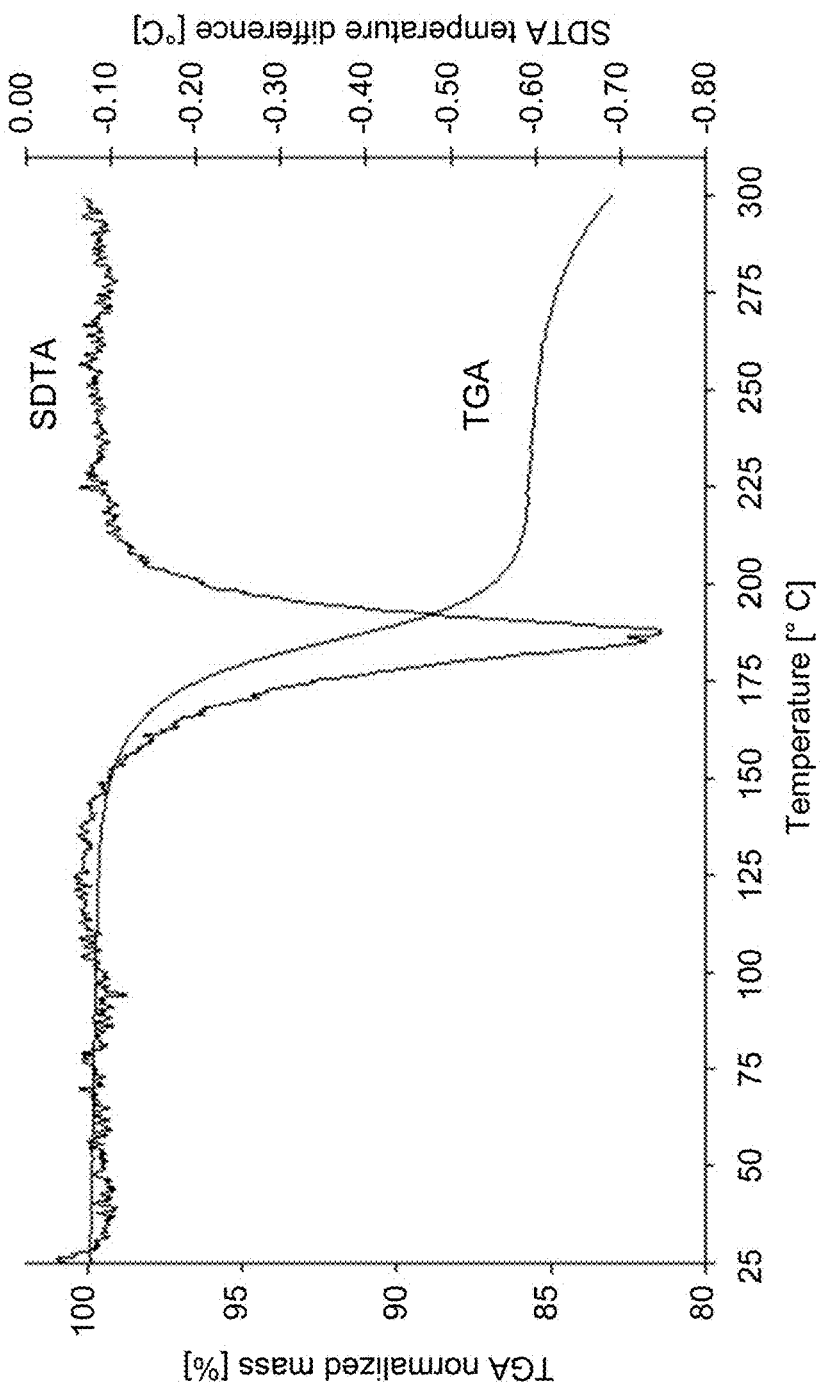
FIG. 4 illustrates the TGA thermogram of Compound 1 Form A.

In another embodiment, Compound 1 Form A is characterized by a TGA thermogram substantially according to FIG. 4.

In another embodiment, Compound 1 Form A is characterized by a DSC thermogram with an endothermic event with an onset at 173.1° C.±0.3° C., more preferably ±0.2° C., most preferably ±0.1° C., and a characterizing endothermic peak at 188.2° C.±0.3° C., more preferably ±0.2° C., most preferably ±0.1° C., followed by a second endothermic event with an onset at 187.1° C.±0.3° C., more preferably ±0.2° C., most preferably ±0.1° C., and a characterizing peak at 192.5° C.±0.3° C., more preferably ±0.2° C., most preferably ±0.1° C. From the analysis of the DSC thermogram, it was concluded that Compound 1 Form A is anhydrous.

Figure 7:
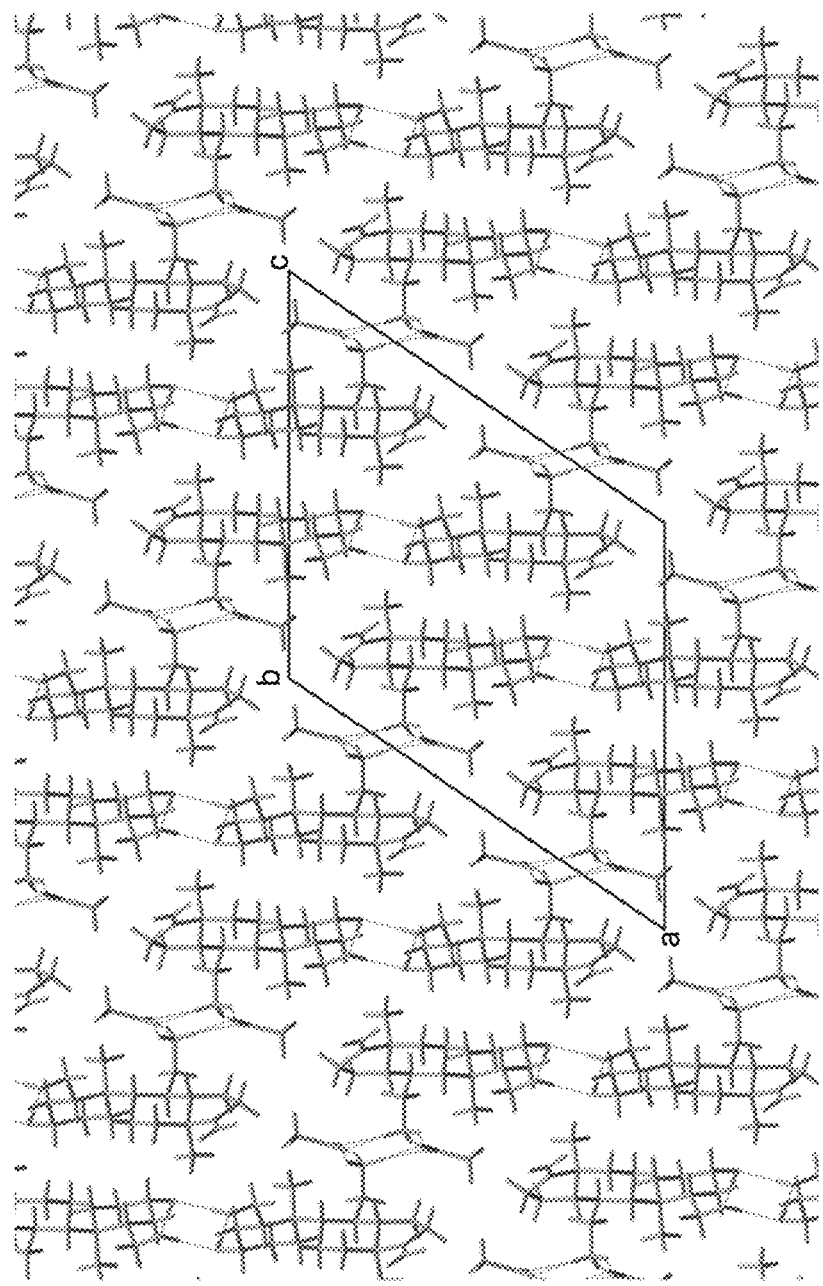
FIG. 7 illustrates the crystal packing and hydrogen bond scheme for of Compound 1 Form A.

In another embodiment, Compound 1 Form A is anhydrous and is stable as indicated by the DSC thermogram in FIG. 3, which shows the acetate is closely associated with Compound 1 and only decomposes at or near the melting point. Compound 1 Form A crystallizes in a chiral monoclinic C2 space group with one anion—cation pair in the asymmetric unit, as seen in FIG. 7. The crystal is held together by a network of intermolecular hydrogen bonds and a Zig-Zag chain is formed, which likely provides the unexpected high stability/melting point of Compound 1.

In another embodiment of the invention, Compound 1 Form A is provided, characterized by the selection of one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four or thirty-five FT-IR transmission peaks selected from the group consisting of 655.0, 668.5, 675.2, 685.4, 774.2, 805.4, 814.4, 824.2, 880.2, 910.3, 937.4, 963.3, 1006.4, 1044.1, 1077.9, 1101.4, 1169.3, 1195.3, 1222.4, 1299.7, 1332.8, 1386.5, 1397.7, 1436.3, 1446.9, 1477.1, 1494.8, 1520.2, 1557.0, 1612.9, 1653.4, 2853.6, 2931.3, 2964.8, 3335.2±3 cm$^{-1}$, more preferably ±2 cm$^{-1}$, and most preferably ±1 cm$^{-1}$.

In another embodiment, Compound 1 Form A is characterized by the following set of FT-IR transmission peaks listed in Table 1:

TABLE 2

FT-IR TRANSMISSION PEAK TABLE
FOR COMPOUND 1 FORM A

| Peak ID | FT-IR transmission (cm$^{-1}$) |
|---|---|
| 1 | 655.0 |
| 2 | 668.5 |
| 3 | 675.2 |
| 4 | 685.4 |
| 5 | 774.2 |
| 6 | 805.4 |
| 7 | 814.4 |
| 8 | 824.2 |
| 9 | 880.2 |
| 10 | 910.3 |
| 11 | 937.4 |
| 12 | 963.3 |
| 13 | 1006.4 |
| 14 | 1044.1 |
| 15 | 1077.9 |
| 16 | 1101.4 |
| 17 | 1169.3 |
| 18 | 1195.3 |
| 19 | 1222.4 |
| 20 | 1299.7 |
| 21 | 1332.8 |
| 22 | 1386.5 |
| 23 | 1397.7 |
| 24 | 1436.3 |
| 25 | 1446.9 |
| 26 | 1477.1 |
| 27 | 1494.8 |
| 28 | 1520.2 |
| 29 | 1557.0 |
| 30 | 1612.9 |
| 31 | 1653.4 |

TABLE 2-continued

FT-IR TRANSMISSION PEAK TABLE FOR COMPOUND 1 FORM A

| Peak ID | FT-IR transmission (cm$^{-1}$) |
| --- | --- |
| 32 | 2853.6 |
| 33 | 2931.3 |
| 34 | 2964.8 |
| 35 | 3335.2 |

Figure 8B:
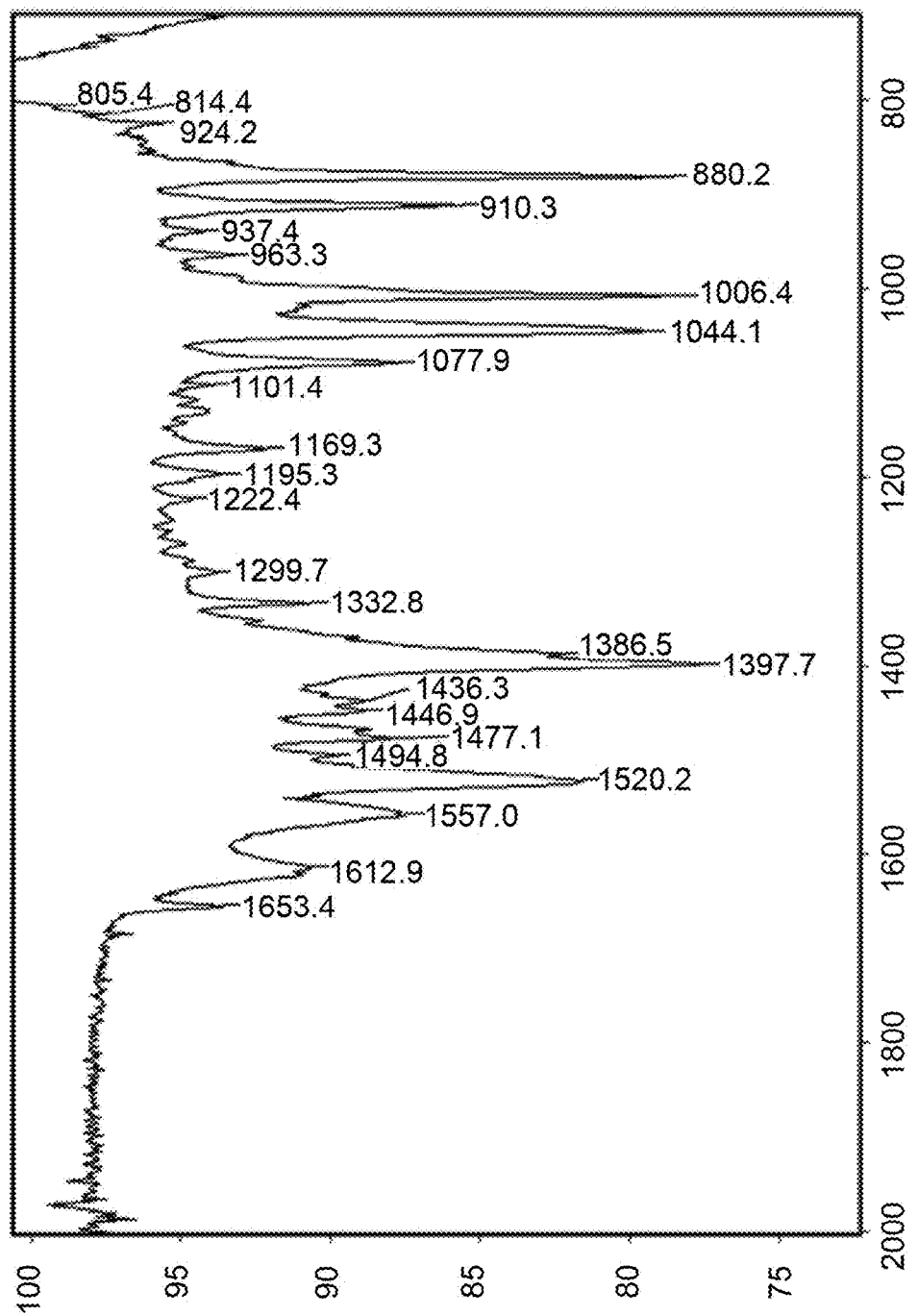
FIG. 8B illustrates the expansion of the full FT-IR spectrum of FIG. 8A, in the fingerprint region of 2000 to 750 $cm^{-1}$.

In another embodiment, Compound 1 Form A is characterized by an FT-IR transmission spectrum substantially according to FIG. 8.

In a preferred embodiment, Compound 1 Form A is characterized by an FT-IR transmission spectrum containing at least one of the following peaks: 910, 1006, 1169 and 1398 cm$^{-1}$±3 cm$^{-1}$, more preferably ±2 cm$^{-1}$, and most preferably ±1 cm$^{-1}$. In a more preferred embodiment, Compound 1 Form A is characterized by an FT-IR transmission spectrum containing at least two of the following peaks: 910, 1006, 1169 and 1398 cm$^{-1}$±3 cm$^{-1}$, more preferably ±2 cm$^{-1}$, and most preferably ±1 cm$^{-1}$.

In another embodiment of the invention, Compound 1 Form A is provided, characterized by the selection of one, two, three, four, five, six, seven, eight, nine, ten, eleven, twelve, thirteen, fourteen, fifteen, sixteen, seventeen, or eighteen Raman shift peaks selected from the group consisting of 2991.2, 2977.3, 2935.3, 2925.8, 2903.7, 2858.3, 1654.3, 1477.9, 1447.7, 1307.9, 1009.8, 945.8, 919.2, 881.7, 743.7, 721.8, 614.8, 423.6±3 cm$^{-1}$, more preferably ±2 cm$^{-1}$, and most preferably ±1 cm$^{-1}$.

In another embodiment, Compound 1 Form A is characterized by the following set of Raman shift peaks listed in Table 1:

TABLE 3

RAMAN SHIFT PEAK TABLE FOR COMPOUND 1 FORM A

| Peak ID | Raman Shift (cm$^{-1}$) |
| --- | --- |
| 1 | 2991.2 |
| 2 | 2977.3 |
| 3 | 2935.3 |
| 4 | 2925.8 |
| 5 | 2903.7 |
| 6 | 2858.3 |
| 7 | 1654.3 |
| 8 | 1477.9 |
| 9 | 1447.7 |
| 10 | 1307.9 |
| 11 | 1009.8 |
| 12 | 945.8 |
| 13 | 919.2 |
| 14 | 881.7 |
| 15 | 743.7 |
| 16 | 721.8 |
| 17 | 614.8 |
| 18 | 423.6 |

Figure 9A:
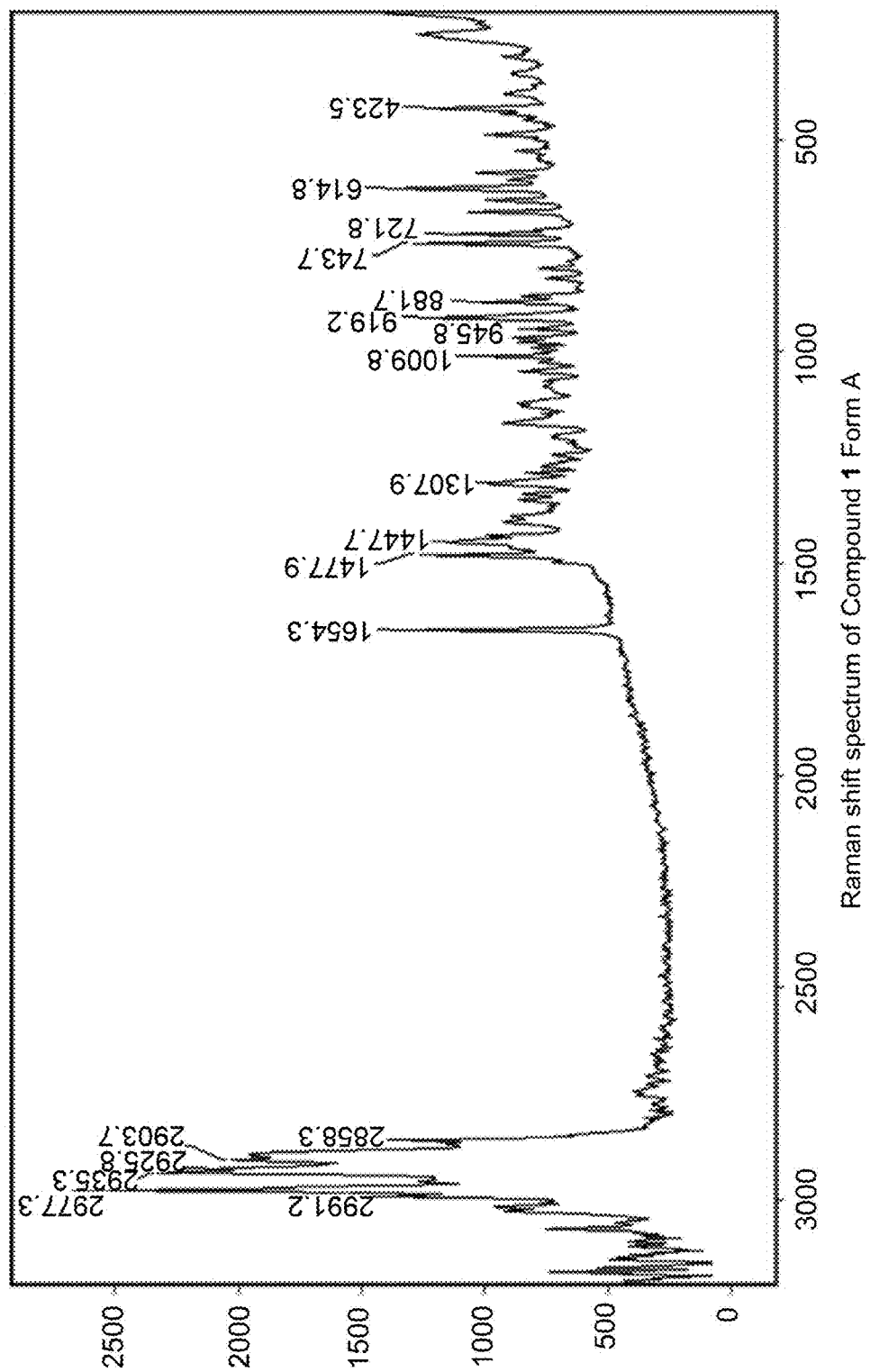
FIG. 9A illustrates the Raman spectrum of Compound 1 Form A.
Figure 9B:
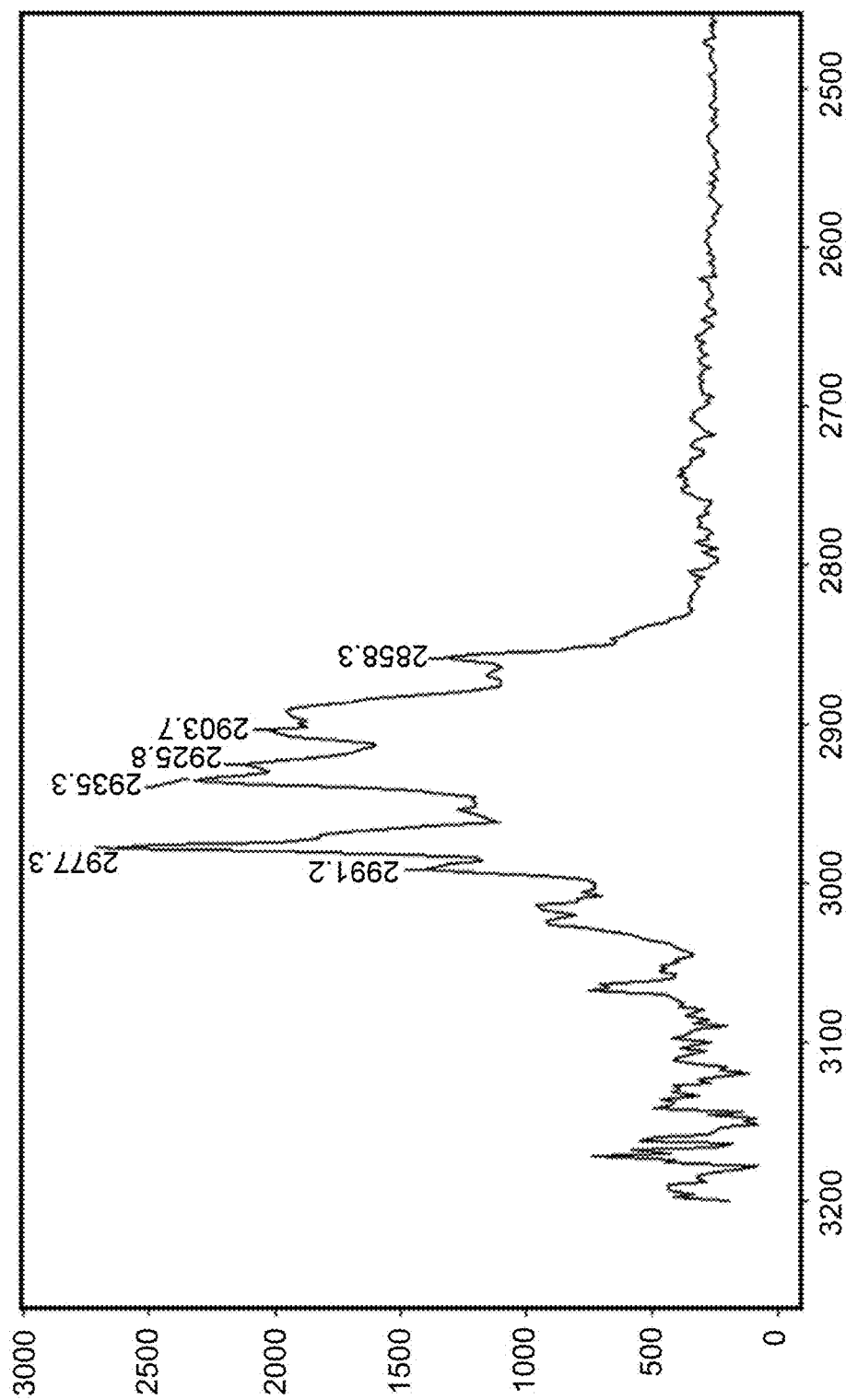
FIGS. 9B and 9C illustrate expansions of the full Raman spectrum of FIG. 9A, in the ranges of ~3200 to ~2450 and ~1900 to ~200 $cm^{-1}$ respectively.
Figure 9C:
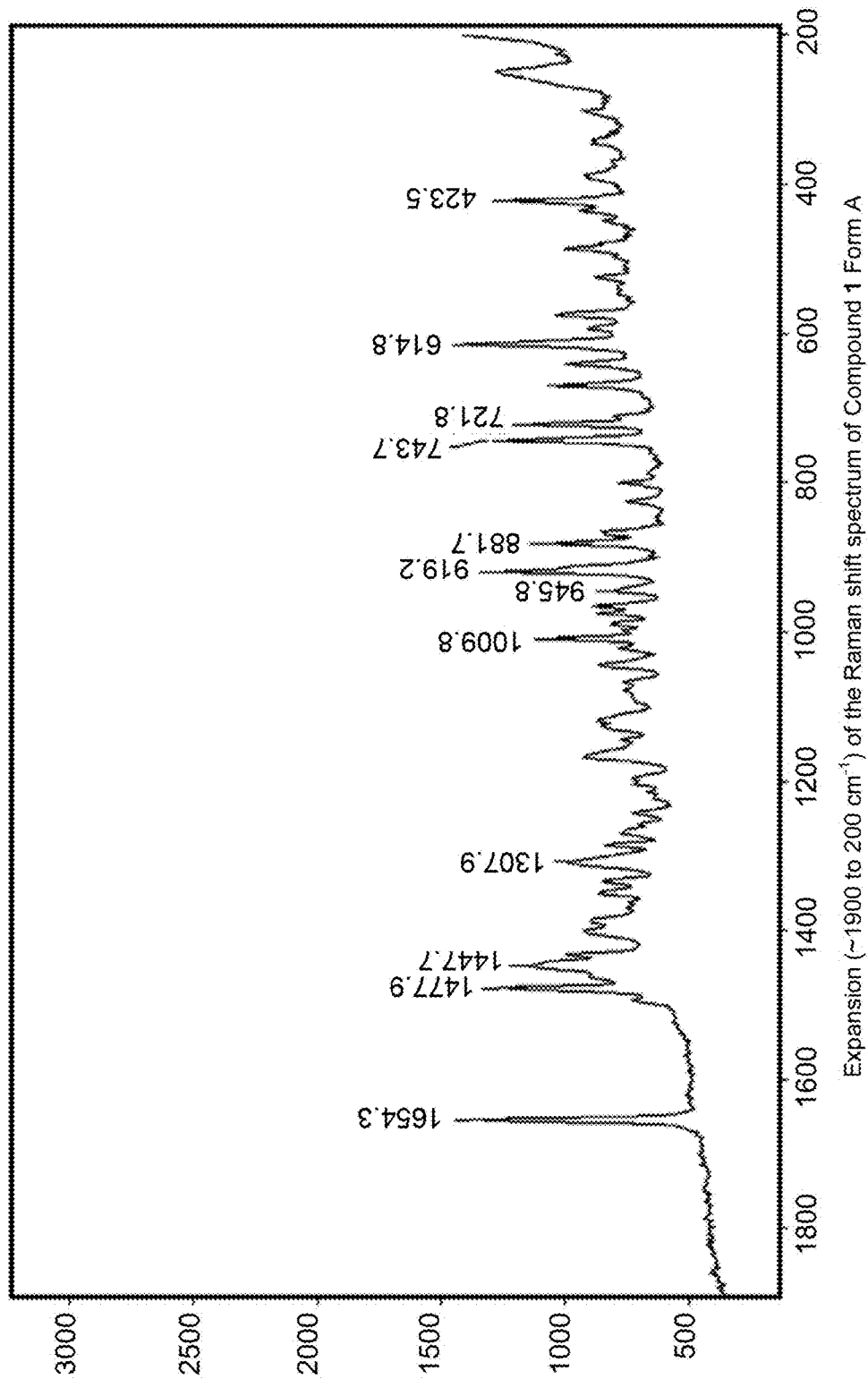

In another embodiment, Compound 1 Form A is characterized by a Raman shift spectrum substantially according to FIG. 9.

In a preferred embodiment, Compound 1 Form A is characterized by a Raman shift spectrum containing at least one of the following peaks: 1654, 1478, 919, 744, 722, and 615 cm$^{-1}$±3 cm$^{-1}$, more preferably ±2 cm$^{-1}$, and most preferably ±1 cm$^{-1}$. In a more preferred embodiment, Compound 1 Form A is characterized by a Raman shift spectrum containing at least two of the following peaks: 1654, 1478, 919, 744, 722, and 615 cm$^{-1}$±3 cm$^{-1}$, more preferably ±2 cm$^{-1}$, and most preferably ±1 cm$^{-1}$.

In another embodiment, Compound 1 Form A, which is anhydrous, is stable and resistant to hydrate formation, to significant amounts of exposure to water as it can be handled in the presence of water (see Example 8 below; 40% water) and exposed to high humidity (75% relative humidity) for 2 days (see General Method J below) without converting to another form, as evidenced by XRPD data (see Example 3 below).

In another embodiment, Compound 1 Form A is in a substantially pure form, and preferably substantially free from other amorphous, crystalline and/or polymorphic forms. In this respect, "substantially pure" means at least about 80%, 85%, 90%, 95%, 96%, 97%, 98%, or 99% of the pure compound. In this respect, "substantially free from other amorphous, crystalline and/or polymorphic forms" means that no more than about 20%, 15%, 10%, 5%, 4%, 3%, 2%, 1% of these other amorphous, crystalline and/or polymorphic forms are present.

In embodiments of the invention, a method for the preparation of Compound 1 Form A is provided, including the steps of preparing a suspension of amorphous Compound 1 in a solvent selected from the group consisting of water, methanol, ethanol, isopropanol, acetone, 2-butanone, ethyl acetate, 1,4-dioxane, tert-butyl methyl ether, tetrahydrofuran, acetonitrile, chloroform, cyclohexane, heptane, toluene, p-xylene, cumene, isopropyl acetate, isopropyl ether, dichloromethane, 2-methoxyethanol, ethyl formate, anisole, 1,2-dimethoxyethane, 2-methyltetrahydrofuran, N,N-dimethylacetamide, 1-butanol, 2-ethoxyethanol, butyl acetate, methyl formate, n-pentane, N,N-dimethylformamide, hexane, 2,2,4-trimethylpentane, diethyl ether, cyclopentane, decane or a mixture thereof, and crystallizing Compound 1 Form A by methods known to those skilled in the art, such as, but not limited to, cooling crystallization, evaporative crystallization by anti-solvent addition, vapor diffusion into liquid crystallization, vapor diffusion onto a solid crystallization, and crystallization by wet milling. In a preferred embodiment, the solvent is selected from the group of water, acetonitrile, methanol, 2-butanone, ethanol, isopropanol, acetone, ethyl acetate, tert-butyl methyl ether, heptane, isopropyl acetate, isopropyl ether, ethyl formate, anisole, 2-methyltetrahydrofuran, 1-butanol, butyl acetate, methyl formate, n-pentane, 2,2,4-trimethylpentane, diethyl ether, decane, or a mixture thereof. In a more preferred embodiment, the solvent is selected from the group of water, acetonitrile, methanol, 2-butanone, ethanol, isopropanol, acetone, ethyl acetate, tert-butyl methyl ether, heptane, isopropyl acetate, ethyl formate, anisole, 1-butanol, butyl acetate, n-pentane, diethyl ether, isopropyl ether, 2-methyltetrahydrofuran, methyl formate, 2,2,4-trimethylpentane, cyclopentane, decane or a mixture thereof.

In certain embodiments, a second solvent (co-solvent or anti-solvent) is used in an amount between 5% and 75% (v/v) with an amount of first solvent between 95% and 25% (v/v), preferably between 10% and 35% (v/v) with an amount of first solvent between 90% and 65% (v/v), more preferably between 15% and 30% (v/v) with an amount of first solvent between 85% and 70% (v/v), and most preferably between 20% and 25% (v/v), with an amount of first solvent between 80% and 75% (v/v). In a preferred embodiment, acetonitrile, heptane, toluene, p-xylene, methylcyclohexane, chloroform, anisole, isopropyl acetate, cyclohexane, or n-pentane is used as a second solvent.

Figure 5:
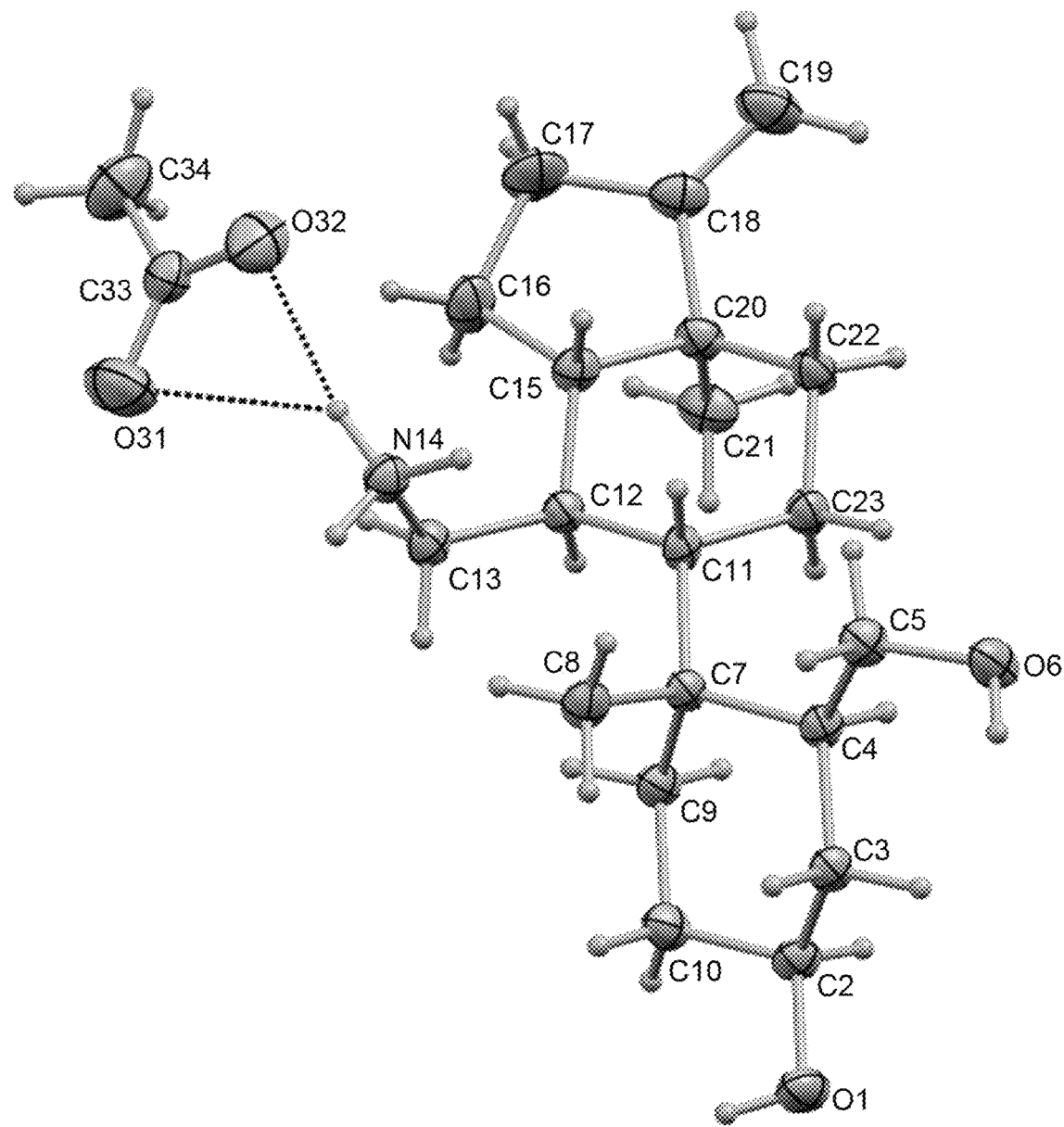
FIG. 5 illustrates the molecular structure of Compound 1 Form A, as determined from single crystal data.

The crystal of Compound 1 Form A of the invention has also been characterized in one aspect relating to the single-crystal structure of Compound 1 Form A as depicted in FIG. 5 and/or FIG. 7 and/or in Table 4:

TABLE 4

CRYSTAL DATA AND STRUCTURE REFINEMENT FOR 1 FORM A.

| | |
|---|---|
| Empirical formula | $C_{20}H_{36}NO_2^+ \cdot C_2H_3O_2^-$ |
| Formula weight | 381.54 |
| Temperature (K) | 200(2) |
| Wavelength (Å) | 0.71073 |
| Crystal system | Monoclinic |
| Space group | C2 |
| Unit cell dimensions (Å) | |
| a [Å] | 19.8179(7) |
| b [Å] | 7.2587(3) |
| c [Å] | 17.8349(6) |
| β [°] | 123.813(3) |
| Volume (Å$^3$) | 2131.64(14) |
| Z | 4 |
| Density (calculated, g/cm$^3$) | 1.189 |
| μ (mm$^{-1}$) | 0.080 |
| F(000) | 840 |
| Crystal size (mm) | 1 × 0.5 × 0.5 |
| Θ range for data collection (°) | 2.5 → 25 |
| Reflections collected | 7037 |
| Independent reflections | 3493 [$R_{int}$ = 0.0493] |
| Completeness to $Θ_{max}$ (%) | 99.2 |
| Absorption correction | semi-empirical from equivalents |
| Max. and min. transmission | 0.9611 and 0.4938 |
| Data/restraints/parameters | 3493/1/265 |
| Goodness-of-fit on F$^2$ | 1.034 |
| Final R indices [I > 2sigma(I)] | R1 = 0.0484, wR2 = 0.1202 |
| R indices (all data) | R1 = 0.0598, wR2 = 0.1291 |
| Largest diff. peak and hole (e/Å$^3$) | 0.243 and −0.202 |

Compound 1 Form B

In another embodiment of the invention, there is disclosed crystalline Compound 1 Form B, characterized by the selection of one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, or thirty-one X-ray powder diffraction peaks selected from the group consisting of 5.5, 9.0, 9.4, 10.5, 12.2, 12.9, 13.2, 14.0, 14.3, 15.4, 16.1, 16.6, 17.0, 18.0, 18.3, 19.0, 20.0, 21.3, 22.8, 24.4, 25.0, 25.8, 26.8, 27.3, 28.1, 28.9, 31.1, 32.5, 33.6, 34.3, 36.2 degrees 2Θ±0.3 degrees 2Θ, more preferably ±0.2 degrees 2Θ, even more preferably ±0.1 degrees 2Θ, most preferably ±0.05 degrees 2Θ.

In another embodiment, Compound 1 Form B can be characterized by the following set of XRPD peaks and, optionally, by the associated intensities listed in Table 5:

TABLE 5

XRPD PEAK TABLE FOR COMPOUND 1 FORM B

| | Embodiment | | | Preferred embodiment | | |
|---|---|---|---|---|---|---|
| Peak ID | Angle (2Θ) | d-Value | Intensity* | Angle (2Θ) | d-Value | Intensity* |
| 1 | 5.5 | 16.0 | M | 5.5056 | 16.0389 | M |
| 2 | 9.0 | 9.8 | M | 8.9784 | 9.8414 | M |
| 3 | 9.4 | 9.4 | L | 9.3738 | 9.4272 | L |
| 4 | 10.5 | 8.4 | L | 10.4954 | 8.4221 | L |
| 5 | 12.2 | 7.2 | M | 12.2283 | 7.2322 | M |
| 6 | 12.9 | 6.8 | H | 12.9263 | 6.8432 | H |
| 7 | 13.2 | 6.7 | H | 13.1691 | 6.7176 | H |
| 8 | 14.0 | 6.3 | L | 14.0469 | 6.2997 | L |
| 9 | 14.3 | 6.2 | L | 14.2556 | 6.2079 | L |
| 10 | 15.4 | 5.8 | M | 15.3571 | 5.7651 | M |
| 11 | 16.1 | 5.5 | L | 16.1173 | 5.4948 | L |
| 12 | 16.6 | 5.3 | L | 16.5638 | 5.3477 | L |
| 13 | 17.0 | 5.2 | L | 17.0462 | 5.1974 | L |
| 14 | 18.0 | 4.9 | H | 18.0374 | 4.9140 | H |
| 15 | 18.3 | 4.8 | M | 18.3289 | 4.8365 | M |
| 16 | 19.0 | 4.7 | H | 18.9616 | 4.6765 | H |
| 17 | 20.0 | 4.4 | H | 19.9729 | 4.4419 | H |
| 18 | 21.3 | 4.2 | M | 21.2924 | 4.1696 | M |
| 19 | 22.8 | 3.9 | L | 22.8307 | 3.8920 | L |
| 20 | 24.4 | 3.7 | L | 24.3507 | 3.6524 | L |
| 21 | 25.0 | 3.6 | L | 24.9971 | 3.5594 | L |
| 22 | 25.8 | 3.4 | L | 25.8342 | 3.4459 | L |
| 23 | 26.8 | 3.3 | L | 26.7691 | 3.3276 | L |
| 24 | 27.3 | 3.3 | L | 27.2716 | 3.2675 | L |
| 25 | 28.1 | 3.2 | L | 28.0939 | 3.1737 | L |
| 26 | 28.9 | 3.1 | L | 28.8820 | 3.0888 | L |
| 27 | 31.1 | 2.9 | L | 31.0503 | 2.8779 | L |
| 28 | 32.5 | 2.8 | L | 32.4944 | 2.7532 | L |
| 29 | 33.6 | 2.7 | L | 33.5513 | 2.6689 | L |
| 30 | 34.3 | 2.6 | L | 34.2825 | 2.6136 | L |
| 31 | 36.2 | 2.5 | L | 36.2378 | 2.4756 | L |

*For normalized intensity values: L = 3-25, M = 25-60, H = 60-100.

Figure 10:
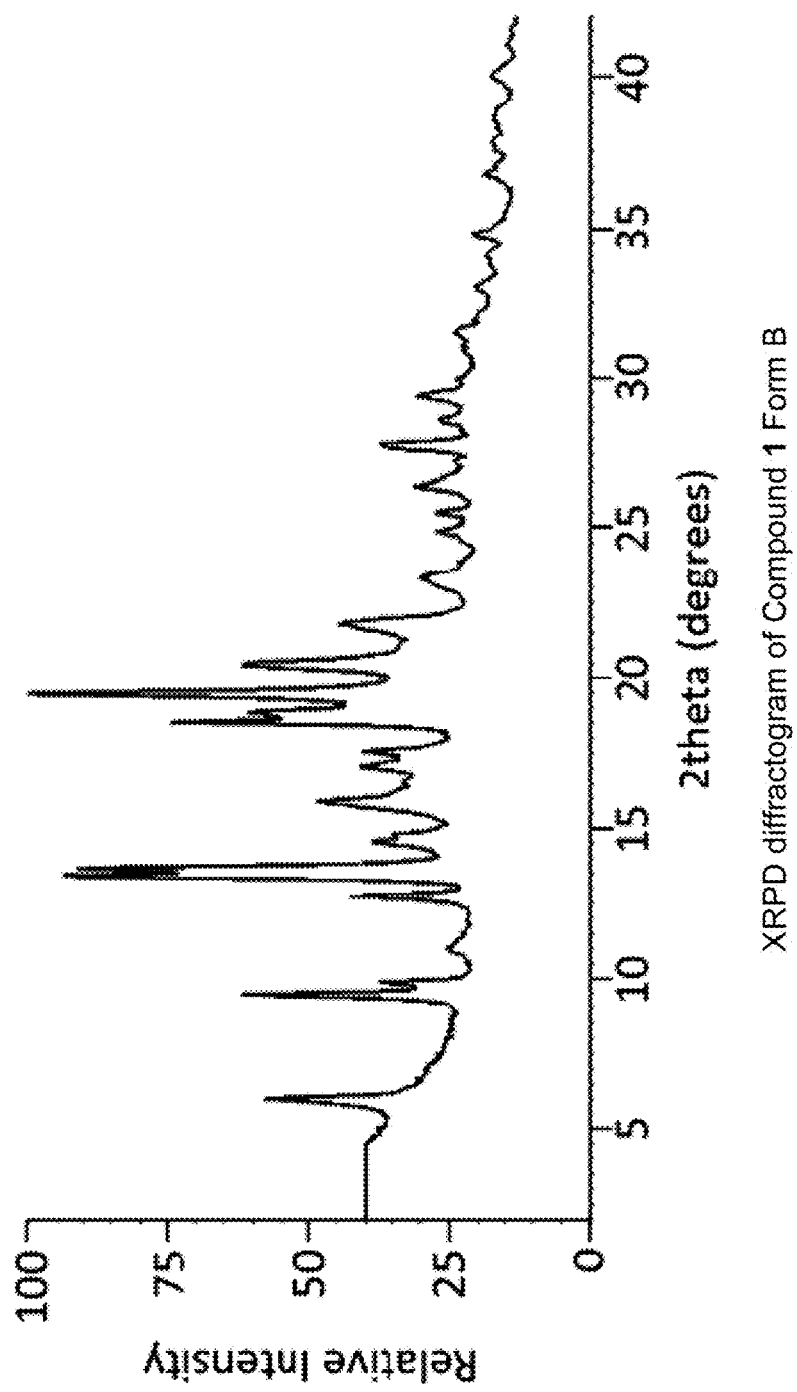
FIG. 10 illustrates the X-Ray Powder Diffraction pattern of Compound 1 Form B.

In another embodiment, Compound 1 Form B is characterized by an XRPD substantially according to FIG. 10.

In a preferred embodiment, Compound 1 Form B is characterized by an XRPD pattern containing at least one of the following peaks: 5.5056, 9.3738 and 12.2283 degrees 2Θ±0.3 degrees 2Θ, more preferably ±0.2 degrees 2Θ, even more preferably ±0.1 degrees 2Θ, most preferably ±0.05 degrees 2Θ. In a more preferred embodiment, Compound 1 Form B is characterized by an XRPD containing at least two of the following peaks: 5.5056, 9.3738 and 12.2283 degrees 2Θ±0.3 degrees 2Θ, more preferably ±0.2 degrees 2Θ, even more preferably ±0.1 degrees 2Θ, most preferably ±0.05 degrees 2Θ.

Figure 11:
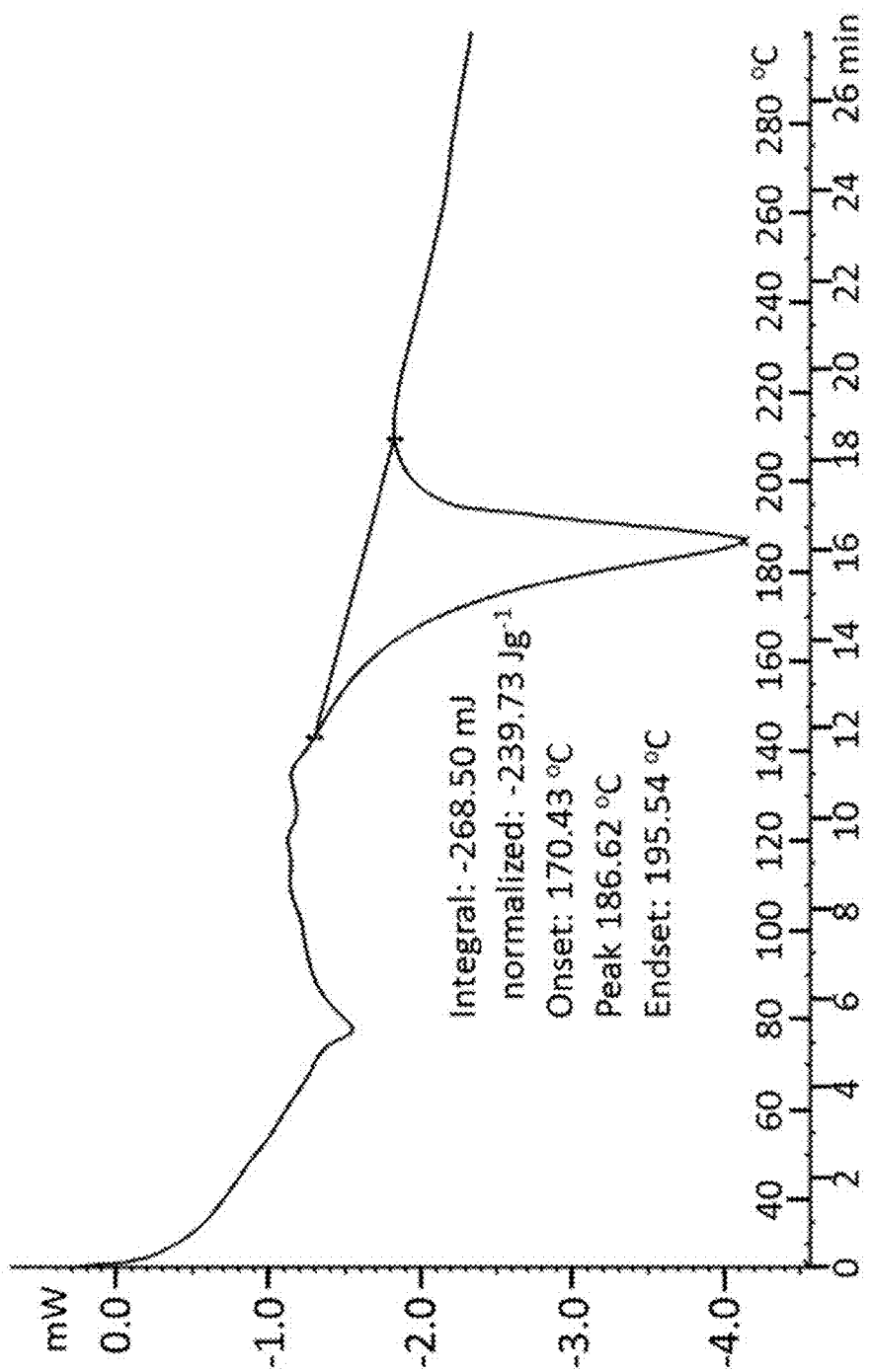
FIG. 11 illustrates the DSC thermogram of Compound 1 Form B.

In another embodiment, Compound 1 Form B is characterized by a DSC substantially according to FIG. 11.

Figure 12:
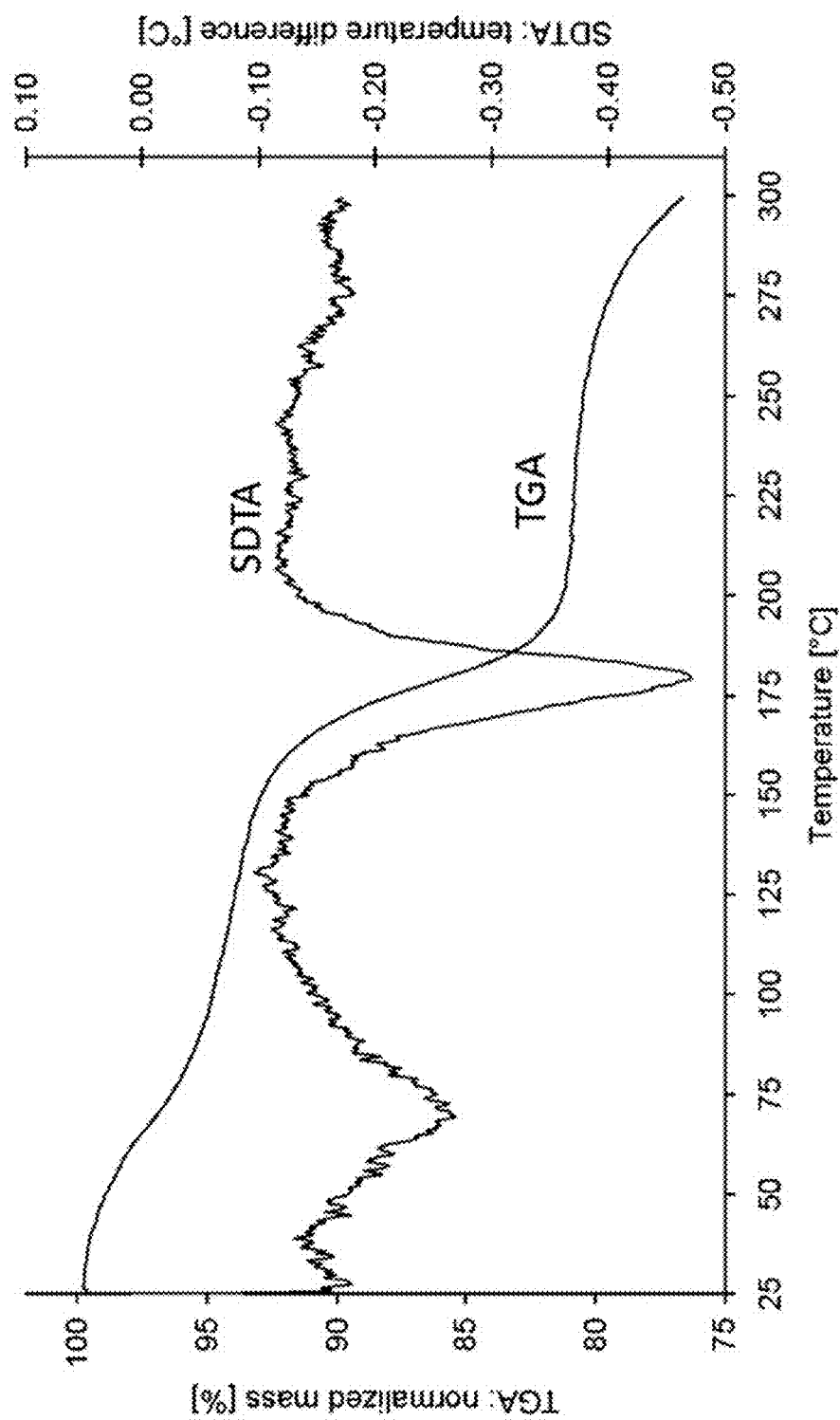
FIG. 12 illustrates the TGA thermogram of Compound 1 Form B.

In another embodiment, Compound 1 Form B is characterized by a TGA substantially according to FIG. 12.

In another embodiment, Compound 1 Form B of the present invention is characterized by DSC with an endothermic event with an onset at 170.4° C.±0.3° C., more preferably ±0.2° C., most preferably ±0.1° C. and a characterizing endothermic peak at 186.6° C.±0.3° C., more preferably ±0.2° C., most preferably ±0.1° C. From thermal analysis, it is concluded that solid Compound 1 Form B is a hydrate.

In another embodiment, Compound 1 Form B is a hydrate.

In another embodiment, Compound 1 Form B is in a substantially pure form, preferably substantially free from other amorphous, crystalline and/or polymorphic forms. In this respect, "substantially pure" relates to at least about 80%, 85%, 90%, 95%, 96%, 97%, 98%, or 99% of the pure compound. In this respect, "substantially free from other amorphous, crystalline and/or polymorphic forms" means that no more than about 20% 15%, 10%, 5%, 4%, 3%, 2%, 1% of these other amorphous, crystalline and/or polymorphic forms are present in the form according to the invention.

The present invention in one aspect relates to a method for the preparation of the crystalline Compound 1 Form B comprising the steps of preparing a suspension of Compound 1 in a solvent selected from the group consisting of water or tetrahydrofuran or mixtures thereof and crystallizing Compound 1 Form B by cooling crystallization, evaporative crystallization by anti-solvent addition, vapor diffusion into liquid crystallization, vapor diffusion onto a solid crystallization, or crystallization by wet milling.

In certain embodiments, a second solvent (co-solvent or anti-solvent) is used in an amount between 5% and 95% (v/v) with an amount of first solvent between 95% and 5% (v/v), preferably between 15% and 85% (v/v) with an amount of first solvent between 85% and 15% (v/v), more preferably between 25% and 75% (v/v) with an amount of first solvent between 75% and 25% (v/v), and most preferably between 35% and 65% (v/v), with an amount of first solvent between 65% and 35% (v/v).

In a preferred embodiment, the solvent is a mixture of water and tetrahydrofuran. In a more preferred embodiment, the solvent is a 1:1 (v/v) mixture of water and tetrahydrofuran.

Pharmaceutical Compositions

Compound 1 Form A and Compound 1 Form B may be formulated as a pharmaceutical composition in a manner similar to the pharmaceutical compositions disclosed in U.S. Pat. Nos. 7,601,874 and 7,999,010. Such pharmaceutical compositions comprise Compound 1 Form A or Compound 1 Form B and one or more pharmaceutically acceptable carriers, wherein the Compound 1 Form A or Compound 1 Form B is present in the composition in an amount that is effective to treat the condition of interest. Typically, the pharmaceutical compositions of the present invention include Compound 1 Form A or Compound 1 Form B in an amount ranging from 0.1 mg to 250 mg per dosage depending upon the route of administration, and more typically from 1 mg to 60 mg. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain—in addition to Compound 1 Form A or Compound 1 Form B—diluents, dispersing and surface-active agents, binders, lubricants, and/or delayed releases agents. One skilled in this art may further formulate Compound 1 Form A or Compound 1 Form B in an appropriate manner, and in accordance with accepted practices, such as those disclosed in Remington's Pharmaceutical Sciences, Gennaro, Ed., Mack Publishing Co., Easton, Pa. (current edition, the relevant sections of which are incorporated herein by reference in their entirety).

Utility and Methods of Administration

Compound 1 and its novel crystalline forms, i.e., Compound 1 Form A and Compound 1 Form B, have activity as SHIP1 modulators and therefore may be used to treat any of a variety of diseases, disorders or conditions in a mammal, preferably a human, that would benefit from SHIP1 modulation. Such diseases, disorders or conditions are disclosed in PCT Published Patent Application Nos. WO 2014/143561 and WO 2014/158654.

Accordingly, an embodiment of the invention is a method modulating SHIP1 activity in a mammal comprising administering an effective amount of Compound 1 Form A or Compound 1 Form B or an effective amount of a composition comprising Compound 1 Form B or Compound 1 Form A to the mammal in need thereof.

Another embodiment is a method for treating a disease, disorder or condition associated with SHIP1 activity in a mammal comprising administering an effective amount of Compound 1 Form A or Compound 1 Form B or an effective amount of a composition comprising Compound 1 Form A or Compound 1 Form B to the mammal in need thereof.

Such methods include administering to a mammal, preferably a human, Compound 1 Form A or Compound 1 Form B in an amount sufficient to treat the disease, disorder or condition. In this context, "treat" includes prophylactic administration. Such methods include systemic administration of Compound 1 Form A or Compound 1 Form B, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parenteral administration, the compounds of the present invention can be prepared in aqueous injection solutions which may contain buffers, antioxidants, bacteriostats, and other additives commonly employed in such solutions.

Methods of Preparation

Representative crystalline forms of Compound 1 of the invention were prepared according to Methods A to J, as described below and subsequently analyzed. Representative crystalline forms of Compound 1 were aged by Method J and subsequently analyzed. It will be appreciated that in the following general methods, solvents used, relative amounts of solvents, and other parameters such as cooling rates, temperatures, times, etc. can be altered to suit needs, up or down by up to 50% without significant change in expected results.

Method A: Crystallization by Slurry Conversion and Evaporative Crystallization

A 26.4 mg aliquot of amorphous solid was solid dosed in a 1.8 mL glass vial. Ethanol was added in defined aliquots (ex. 100 µL) until about 50% of the solid had dissolved (200 µL final volume). The vial was incubated at elevated temperature for a period of time followed by cooling to ambient temperature. After prolonged incubation, the solid was separated from the liquid by centrifugation. The solid was dried under ambient conditions and analyzed by XRPD. The solvent was further evaporated under ambient conditions and the remaining solids analyzed by XRPD.

By similar techniques, a person skilled in the art would be able to obtain similar results utilizing the solvents methanol, acetone, isopropanol, ethyl acetate, 2-butanone, tert-butyl methyl ether, 1,4-dioxane, acetonitrile, tetrahydrofuran, cyclohexane, chloroform, toluene, heptane, cumene, p-xylene, anisole, isopropyl acetate, and 1,2-dimethoxyethane.

Method B: Crystallization by Evaporative Crystallization

A 20.4 mg aliquot of amorphous solid was dissolved in a mixture of methanol and toluene (50:50, (vv)), in a vial. The vial was heated to elevated temperature and the solution filtered through a 0.45 µm PTFE filter, as needed, to obtain a clear solution. Subsequently, the solvents were removed by evaporation at 500 mbar vacuum until completely dry (50 hr). Solid was collected from the vials and analyzed by XRPD.

By similar techniques, a person skilled in the art would be able to obtain similar results utilizing the solvent pairs tetrahydrofuran/ethanol, water/acetonitrile, 1-butanol/isopropyl ether, isopropanol/dichloromethane, tert-butyl methyl ether/2-methoxyethanol, cumene/1,2-dimethoxyethane, heptane/ethanol, chloroform/ethyl formate and water/1,4-dioxane.

Method C: Crystallization by Anti-Solvent Addition

A 39.7 mg aliquot of amorphous solid was dissolved in a water (100 µL). Acetonitrile (400 µL), as anti-solvent, was added to the vial of the clear solution. Precipitated solid was collected by centrifugation, dried under ambient conditions and analyzed by XRPD.

By similar techniques, a person skilled in the art would be able to obtain similar results utilizing the solvent/anti-solvent pairs ethanol/heptane, dichloromethane/toluene, tetrahydrofuran/p-xylene, isopropanol/methylcyclohexane, methanol/chloroform, ethanol/anisole, 2-methyltetrahydrofuran/isopropyl acetate, and 1,4-dioxane/cyclohexane, N,N-dimethylacetamide/n-pentane.

Method D: Crystallization by Cooling

A solution of amorphous solid (121 mg/mL) was prepared in a solvent mixture of methanol and acetonitrile (400 µL, 50/50 (v/v)), using 40.7 mg of amorphous solid. The slurry mixture was heated, with stirring, to elevated temperature and passed through a preheated 0.45 µm PTFE filter to provide a clear solution. The solution was subjected to a cooling profile, for example, cooling to 5° C. with a cooling rate of 1° C./minute. The sample was kept cold for an extended period before the precipitated solid was separated from the liquid. The solid was dried under ambient conditions and analyzed by XRPD.

By similar techniques, a person skilled in the art would be able to obtain similar results utilizing the solvent mixtures ethyl formate/1-butanol, 2-methyltetrahydrofuran/cumene, isopropanol/chloroform, isopropyl acetate/ethanol, 1,4-dioxane/tert-butyl methyl ether, p-xylene/dichloromethane, 2-methoxyethanol/1,2-dimethoxyethane, and cyclohexane/ethanol.

Method E: Crystallization by Thermocyclin

A 27.7 mg aliquot of amorphous solid was solid dosed in a 1.8 mL vial and isopropanol (200 µL) was added at ambient temperature. The vial was subjected to a temperature profile of heating and cooling between high (ex. 50° C.) and low (5° C.) temperatures, for three distinct cycles, for example, each heating cycle was at 10° C./hr while the cooling cycles were at −20° C./hr, −10° C./hr and −5° C./hr, for each cycle respectively, finishing at ambient temperature. Upon completion of the thermo-profile, the resulting solid was separated from the liquid by centrifugation and dried under ambient conditions before being analyzed by XRPD.

By similar techniques, a person skilled in the art would be able to obtain similar results utilizing the solvents 1,2-dimethoxyethane, acetonitrile, ethyl formate, 2-ethoxyethanol, tetrahydrofuran, p-xylene, isopropanol, butyl acetate, tert-butyl methyl ether, 1,4-dioxane, methanol/water (60 to 80/40 to 20 (v/v)), acetonitrile/water (80 to 98/20 to 2 (v/v)), and isopropanol/water (80 to 90/20 to 10 (v/v)).

Method F: Crystallization by Vapor-Diffusion-Onto-Solid

A 1.8 mL vial was charged with 20.0 mg of amorphous solid. The vial was left open and placed in a larger container with a small amount (2 mL) of 1,4-dioaxne as the anti-solvent. After an extended period of exposure to the solvent vapors at room temperature, the resulting solid was collected and analyzed by XRPD.

By similar techniques, a person skilled in the art would be able to obtain similar results utilizing the anti-solvents 1,2-dimethoxyethane, methyl formate, isopropyl ether, n-pentane, dichloromethane, isopropanol, acetonitrile, chloroform and toluene.

Method G: Crystallization by Vapor-Diffusion-Into-Solution

A saturated solution was generated by dissolving 46.1 mg aliquot of amorphous solid, in a vial, in water (100 µL). The vial was left open and was placed in a larger closed container with a small amount (2 mL) of acetonitrile, as the anti-solvent. After an extended period of incubation, the resulting precipitated solid was separated from the liquid by centrifugation, dried under ambient conditions and analyzed by XRPD.

By similar techniques, a person skilled in the art would be able to obtain similar results utilizing the solvent/anti-solvent pairs methanol/heptane, tetrahydrofuran/hexane, ethanol/chloroform, isopropanol, 2,2,4-trimethylpentane, dichloromethane/diethyl ether, 1,4-dioxane/tert-butyl methyl ether, N,N-dimethylformamide/toluene, tetrahydrofuran/cyclopentane, and dichloromethane/n-pentane.

Method H: Crystallization by Single-Solvent Drop Grinding

A stainless steel RETSCH® grinding container was charged with a 19.2 mg aliquot of amorphous solid and ethyl acetate (10 µL) was added. The vial was mounted in a RETSCH® MM301 ball mill and ground at a defined frequency (ex. 30 Hz). After grinding for a defined time (ex. one hour), the resulting solid was collected and analyzed by XRPD.

By similar techniques, a person skilled in the art would be able to obtain similar results utilizing the solvent isopropanol, chloroform, decane, cumene, anisole, acetonitrile, cyclohexane, p-xylene, and 1,2-dimethoxyethane Method I: Quantitative Solubility Assessment and Crystallization The solubility of 1 in a solvent or solvent mixture was determined at room temperature. A 20 mg aliquot of 1 (amorphous) was weighed in a standard 1.8 mL HPLC vial. Subsequently, isopropanol (200 µL) was added and the vial was left to equilibrate at room temperature with continuous stirring. After 24 hours, the solid was separated from the liquid by centrifugation and analyzed by XRPD. Subsequently the remaining liquid phase was further filtered through a 0.45 µm PTFE filter to remove any particulate matter. The concentration of the 1 in solution was determined by HPLC-DAD analysis using a calibration curve made from two independent stock solutions of the 1 prepared in 0.1% TFA in water/acetonitrile (50:50).

By similar techniques, a person skilled in the art would be able to obtain similar results utilizing a variety of solvents.

Method J: Accelerated Aging Analysis by XRPD

Samples collected from the crystallization conditions were subjected, as is, to accelerated aging conditions of 40° C. and 75% relative humidity for 48 hours, via standard methods and analyzed by XRPD.

The following Examples are provided for purposes of illustration, not limitation. In summary, the following Examples disclose the preparation, analysis and characterization of Compound 1 Form A and Compound 1 Form B of the invention. One of ordinary skill in the art understands that experimental differences may arise due to differences in instrumentation, sample preparation, or other factors.

Example 1

Preparation of Compound 1 Form A for XRPD, DSC and TGA Analysis

Compound 1 Form A was generated through a modified Method B procedure. Amorphous Compound 1 (100 mg)

was suspended in a 5:1 (v/v) mixture of methanol (250 μL) and of isopropyl acetate (50 μL). The mixture was heated up to 75° C. and kept at this temperature for about 30 minutes until all remaining material was dissolved. Heating was subsequently removed and the mixture left to slowly cool to room temperature. After several hours, white material started to precipitate. After 24 hours, white solid was filtered, washed using cold isopropyl acetate and air-dried for about 24 hours. Dry solid was manually ground, by mortar and pestle, yielding a fine white powder, i.e., Compound 1 Form A, in the mortar, which was analyzed by XRPD, DSC and TGA.

Example 2

Preparation of Compound 1 Form B for XRPD, DSC, and TGA Analysis

Compound 1 Form B was generated through a modified Method B procedure. Amorphous Compound 1 (20.4 mg) was suspended in water (104 μL) containing trifluoroethanol (0.01% (v/v)). The mixture was kept at 21° C. and stirred using a stirring bar for 115 hours. The solvent was slowly evaporated under ambient conditions and remaining solid was left for drying. The dry material was manually ground, by mortar and pestle, yielding a fine white powder in the mortar, i.e., Compound 1 Form B, which was analyzed by XRPD, DSC and TGA.

Example 3

X-Ray Diffraction Spectrometry Experimental Conditions

Dry solid samples from Examples 1 and 2, were transferred into a boron-glass capillary with 0.3 mm outer diameter. The capillary was mounted on the goniometer head and placed in the D8 Advance Bruker-AXS Diffractometer equipped with solid state LynxEye detector. The capillary was spinning during data recording, at 15 rpm. The XRPD platform was calibrated using Silver Behenate for the long d-spacings and Corundum for the short d spacings.

Data collection for Compound 1 Form A and Compound 1 Form B, were carried out, in transmission mode, at ambient conditions (~23° C. and ~100 kPa) using monochromatic CuK$_{\alpha1}$ radiation (1.540568 Å) in the 2θ region between 4° and 45°, with an exposure time of 90 s for each frame and 0.016° increments. No additional corrections were made during data collection.

Peak selection was performed using DIFFRAC$^{plus}$ EVA software package (Bruker-AXS, 2007), using a second derivative method working on data prepared by Savitzky-Golay (Savitzky, A. & Golay, M. J. E. (1964) *Anal. Chem.* 36, 1627) smoothing filter with the following criteria:
 1. Peak width: The algorithm uses 5 to 57 data points centered on the point of interest, and a peak is selected from the second derivate if the peak width lays within the range FWHM<Peak width<4×FWHM. Peak widths for 1 Form A and 1 Form B were 0.2 and 0.3°, respectively.
 2. Threshold: Based on the comparison of the computed maximum of the peak with the middle of the chord joining 2 inflection points of both sides of maximum. According to Equation 1, a peak was accepted if $I_P$ was greater than the intensity at chord center ($I_M$) plus a factor comprising a threshold value of 1.0 multiplied by the square root of $I_M$, as described in the software manual (DIFFRAC$^{PLUS}$ EVA Manual (2007) Bruker-AXS, Karlsruhe):

$$I_P > I_M + T \times \sqrt{I_M} \quad \text{(Equation 1)}$$

Where: $I_P$=peak intensity; $I_M$=intensity at chord center; T=threshold.

The XRPD diffractogram from Example 3 are shown in FIG. 2 for Compound 1 Form A and FIG. 10 for Compound 1 Form B, and are indicative of diffractograms generated from material for Compound 1 Form A and Compound 1 Form B performed by alternative crystallization methods.

In addition, crystalline material of Compound 1 Form A was subjected to Method J and analyzed by XRPD and found to yield diffractograms that were equivalent to FIG. 2.

The diffractogram presented in FIG. 1 was recorded on D8 Discover Bruker-AXS diffractometer using Cu IC, radiation (1.54178 Å) equipped with 2D GADDS detector in transmission mode. The sample of amorphous Compound 1 was placed in the flat transmission sandwich-like 4.5 mm diameter sample holder protected by X-Ray transparent mylar foil. During the measurement sample was oscillated in x,y direction (perpendicular to the primary beam) with 1.75 mm radius. Data collection was carried out in two frames 1.5<2θ<21.5° and 19.5<2θ<41.5° and separately integrated with step size 0.04°. The final powder pattern was obtained by merging both frames using area between 19.5<2θ<21.5° as common share. Peaks were analyzed as described above.

Example 4

Single-Crystal X-Ray Diffraction Experimental Conditions

A 1-dram vial was charged with Compound 1 (30 mg) and diluted with methanol (0.3 mL). To the resulting solution was added methyl tert-butyl ether (0.4 mL) and the vial sealed and allowed to stand at room temperature for 2 weeks. These conditions afforded colorless crystals approximately 0.5 cm in length as overlapping, layered plates, approximately 1 mm in thickness. The remaining solvent was removed by decanting and the crystals were allowed to dry at room temperature overnight Suitable single crystal was selected and mounted on a Mitegen Micromount with a UV curable adhesive, which was then mounted on an X-ray diffraction goniometer (Bruker SMART X2S crystallographic system, Delft, The Netherlands). X-ray diffraction data were collected for these crystals at −73° C., using monochromatized (Doubly Curved Silicon Crystal) MoK$_\alpha$ radiation (0.71073 Å), from a sealed MicroFocus tube. Generator settings were 50 kV, 1 mA.

Data were acquired using three sets of Omega scans at different Phi settings and the frame width was 0.5° with an exposure time of 5.0 s. The detailed data collection strategy was as follows:

| Detector distance: 40 mm; Detector swing angle (fixed 2 Theta): −20° | | | | |
| --- | --- | --- | --- | --- |
| Run | Omega (start) | Omega (end) | Phi | Frames |
| 1 | −20.0 | 160.0 | 0 | 360 |
| 2 | −20.0 | 100.0 | 120.0 | 240 |
| 3 | −20.0 | 40.0 | 240.0 | 120 |

Of the 7287 reflections that were collected, 3603 were unique ($R_{int}$=0.047); equivalent reflections (excluding Friedel pairs) were merged. Data were integrated using the Bruker SAINT software package (Version 7.68A. Bruker AXS Inc., Madison, Wis., USA (1997-2010)). The linear absorption coefficient, μ, for Mo-Kα radiation is 0.80 cm$^{-1}$. Data were corrected for absorption effects using the multi-scan technique (SADABS), with minimum and maximum transmission coefficients of 0.534 and 0.961, respectively (SADABS. Bruker Nonius area detector scaling and absorption correction—V2008/1, Bruker AXS Inc., Madison, Wis., USA (2008)). The data were corrected for Lorentz and polarization effects.

The structure was solved by direct methods (SIR97—Altomare A., Burla M. C., Camalli M., Cascarano G. L., Giacovazzo C., Guagliardi A., Moliterni A. G. G., Polidori G., Spagna R. (1999) J. Appl. Cryst. 32, 115-119). All non-hydrogen atoms were refined anisotropically. All O—H and N—H hydrogen atoms were located in difference maps and refined isotropically. All other hydrogen atoms were placed in calculated positions. No attempt was made to ascertain the correct absolute configuration of the molecule, due to the weak anomalous signal from the sample. The final cycle of full-matrix least-squares refinement (function minimized was $\Sigma w\ (F_o^2 - F_c^2)^2$) on $F^2$ was based on 3603 reflections and 268 variable parameters and converged (largest parameter shift was 0.00 times its esd) with unweighted and weighted agreement factors of:

$R1 = \Sigma ||F_o| - |F_c|| / \Sigma |F_o| = 0.047, I > 2\sigma(I)$ $wR2 = [\Sigma(w(F_o^2 - F_c^2)^2) / \Sigma w(F_o^2)^2]^{1/2} = 0.135$, all data The standard deviation of an observation of unit weight $([\Sigma w(F_o^2 - F_c^2)^2 / (N_o - N_v)]^{1/2}$, where $N_o$=number of observations and $N_v$=number of variables) was 1.07. The weighting scheme was based on counting statistics. The maximum and minimum peaks on the final difference Fourier map corresponded to 0.25 and –0.18 e$^-$/Å$^3$, respectively. Neutral atom scattering factors were taken from Cromer and Waber (Cromer, D. T. & Waber, J. T.; "International Tables for X-ray Crystallography", Vol. IV, The Kynoch Press, Birmingham, England, Table 2.2 A (1974)). Anomalous dispersion effects were included in Fcalc (Ibers, J. A. & Hamilton, W. C.; Acta Crystallogr., 17, 781 (1964)); the values for Δf' and Δf" were those of Creagh and McAuley (Creagh, D. C. & McAuley, W. J.; "International Tables for Crystallography", Vol C, (A. J. C. Wilson, ed.), Kluwer Academic Publishers, Boston, Table 4.2.6.8, pages 219-222 (1992)). The values for the mass attenuation coefficients are those of Creagh and Hubbell (Creagh, D. C. & Hubbell, J. H.; "International Tables for Crystallography", Vol C, (A. J. C. Wilson, ed.), Kluwer Academic Publishers, Boston, Table 4.2.4.3, pages 200-206 (1992)). All refinements were performed using the SHELXL-9710 via the WinGX11 interface (Sheldrick, G. M. 2008. Acta Cryst. A64, 112-122, WinGX—V1.70—Farrugia, L. J.; J. Appl. Cryst., 32, 837 (1999)).

Data was visualized using Mercury CSD 2.0 (Macrae, C. F., Bruno, I. J., Chisholm, J. A., Edgington, P. R., McCabe, P., Pidcock, E., Rodriguez-Monge, L., Taylor, R., van de Streek, J. & Wood, P. A. (2008). J. Appl. Cryst. 41, 466). A representation of the crystal structure from this Example is shown in FIGS. 5 and 7. The details of this crystal structure were used in Example 5.

Example 5

Comparison of Compound 1 Form A experimental XRPD and Single-Crystal-Derived Simulated XRPD Diffractograms The simulated powder data from the single crystal of Compound 1 Form A, described in Example 4, was performed using Mercury Package, version 3.5.1 (Macrae, C. F., Bruno, I. J., Chisholm, J. A., Edgington, P. R., McCabe, P., Pidcock, E., Rodriguez-Monge, L., Taylor, R., van de Streek, J. & Wood, P. A. (2008). J. Appl. Cryst. 41, 466). The peak positions were calculated based on the crystal symmetry and unit cell parameters, while the peak intensities were calculated from electron density based on the atom positions within the asymmetric unit. The following restraints were applied. The radiation used was CuK$_{\alpha1}$ (1.54056 Å). The Lorentz-polarization correction typical for a laboratory X-ray source with the fixed slit widths. Neither absorption nor background correction was included. All non-hydrogen atoms were assumed to have isotropic atomic displacement parameters ($U_{iso}$) of 0.05 Å$^2$. Hydrogen atoms for which 3D coordinates are taken into account and assigned $U_{iso}$ values of 0.06 Å$^2$. The powder pattern simulator was allowed to take site occupation factors into account to correct the patterns generated for disordered structures read from CIF and SHELX Res files. All reflections have a symmetric pseudo-Voight peak shape with a full width half maximum of 0.1 degree 2θ, corresponding to D8 Advance Resolution.

Figure 6:
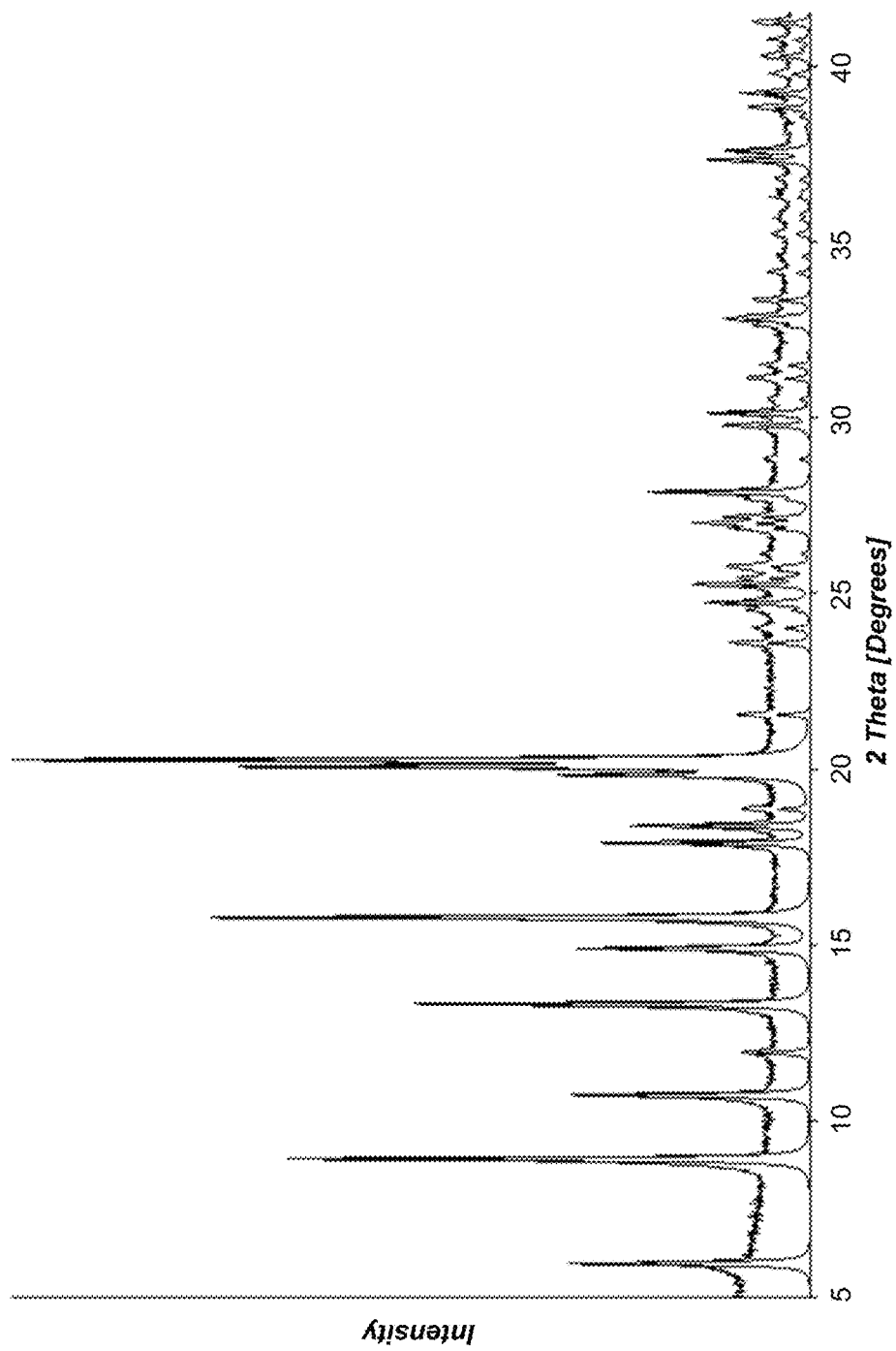
FIG. 6 illustrates the comparison between the simulated powder diffraction pattern and the experimentally derived powder diffraction pattern of Compound 1 Form A.

For comparison of the simulated powder pattern for the single crystal data with the experimental one, both patterns were converted in (x,y) ASCII files and overlaid. No other additional action was taken. FIG. 6 depicts the comparison of Compound 1 Form A experimental XRPD and single-crystal-derived simulated XRPD diffractograms.

Example 6

Thermal Analysis Experimental Conditions

Compound 1 Form A and Compound 1 Form B material from Examples 1 and 2, respectively, were used for thermal analysis.

DSC Analysis: Melting properties were obtained from DSC thermograms, recorded with a heat flux DSC822e instrument (Mettler-Toledo GmbH, Switzerland). The DSC822e was calibrated for temperature and enthalpy with a small piece of indium (m.p.=156.6° C.; ΔH$_f$=28.45 J/g). Samples were sealed in standard 40 microliter aluminum pans and heated in the DSC from 25° C. to 300° C., at a heating rate of 10° C./min. Dry N$_2$ gas, at a flow rate of 50 ml/min, was used to purge the DSC equipment during measurement. Representative DSC data from Example 3 can be found in FIG. 3 for Compound 1 Form A and FIG. 11 for Compound 1 Form B and are indicative of DSC data generated from material for Compound 1 Form A and Compound 1 Form B performed by alternative crystallization methods.

Figure 13:
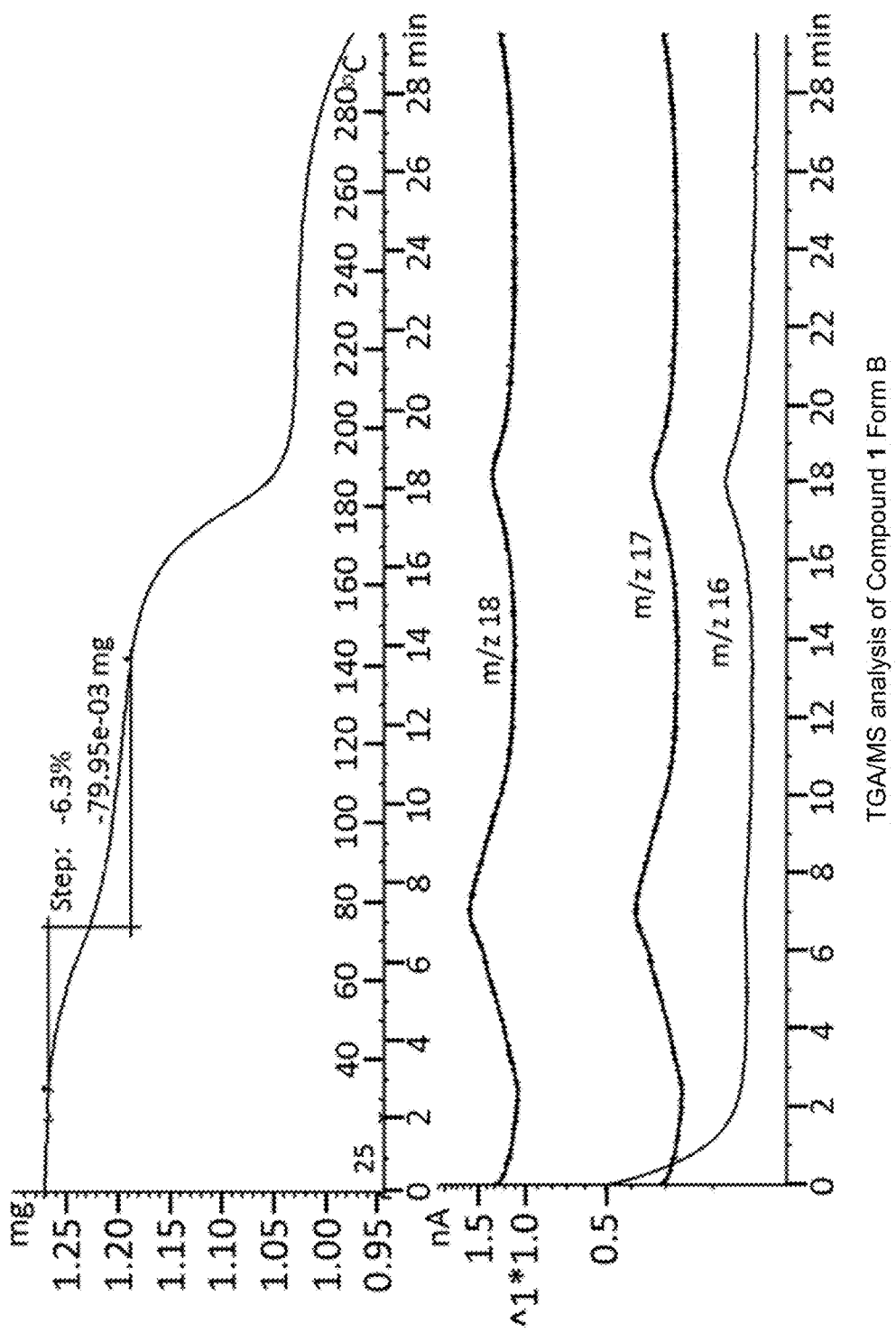
FIG. 13 illustrates the TGA/MS analysis of Compound 1 Form B.

TGA/MS Analysis: Mass loss due to solvent or water loss from the crystals, from Examples 1 and 2, were determined by TGA/SDTA analysis. Monitoring of the sample weight, during heating in a TGA/SDTA851e instrument (Mettler-Toledo GmbH, Switzerland), resulted in a weight vs. temperature curve for each sample. The TGA/SDTA curves for Compound 1 Form A and Compound 1 Form B are in FIGS. 4 and 12, respectively and are indicative of TGA/SDTA data generated from material for Compound 1 Form A and Compound 1 Form B performed by alternative crystallization methods. The TGA/SDTA851e was calibrated for temperature with indium and aluminum. Samples, from Examples 1 and 2, were weighed into 100 μL aluminum crucibles and sealed. The seals were pin-holed and the crucibles heated in the TGA from 25° C. to 300° C. at a heating rate of 10° C./min. Dry N$_2$ gas was used for purging. TGA/MS data for Compound 1 Form B is in FIG. 13 and is indicative of TGA/MS data generated from material for Compound 1 Form B performed by alternative crystallization methods.

Example 7

Crystallization of Compound 1 Form A by Method D

A solution of about 100 mg/mL of Compound 1 was prepared using 39.4 mg of amorphous Compound 1 and 400 µL of an isopropyl acetate/ethanol (50/50 (v/v)) solvent mixture at ambient temperature in a 1.8 mL vial. The solution was heated to 60° C., with a heating rate of 10° C./min, and stirred at 30 rpm, using a Teflon®-coated magnetic stirring bar with dimensions 7 mm in length and 2 mm in width, and subsequently passed through a preheated 0.45 µm PTFE filter to provide a clear solution. The solution was kept at 60° C. for one hour and then cooled to 5° C. with a rate of 1° C./hour. The solution was constantly stirred, as above. The solution was kept at 5° C. for 48 hours and then precipitated solid was collected by centrifugation (3000 rpm for 10 minutes) followed by solvent removal by Pasteur pipette. Solids were dried under ambient conditions and analyzed by XRPD.

Example 8

Crystallization of Compound 1 Form A by Method E 20.0 mg of amorphous Compound 1 was solid dosed in a 1.8 mL vial and 100 µL of a methanol/water mixture (60/40 (v/v)) was added at ambient temperature. The solution was subjected to a temperature profile of heating and cooling between 50° C. and 5° C. for three cycles, each heating cycle was at 10° C./hr while the cooling cycles were at −20° C./hr, −10° C./hr and −5° C./hr, for each cycle, respectively, finishing at ambient temperature. During the entire experiment the mixture was stirred at 30 rpm using a magnetic stirrer and a TEFLON®-coated magnetic stirring bar with dimensions 7 mm in length and 2 mm in width.

Upon completion of the thermo-profile, the solid was collected by centrifugation (3000 rpm for 10 minutes) followed by solvent mixture removal by Pasteur pipette and dried under ambient conditions for one hour, before being analyzed by XRPD.

Example 9

Crystallization of Compound 1 Form A by Method G 41.2 mg of amorphous Compound 1 was solid dosed into a 1.8 mL vial and dissolved in isopropanol (600 µL). The vial was left open and placed in a larger closed container with 2 mL of 2,2,4-trimethylpentane, antisolvent, which was sealed and left for 14 days. The precipitated solid was collected by centrifugation (3000 rpm for 10 minutes) followed by solvent mixture removal by Pasteur pipette and dried under ambient conditions for one hour, before being analyzed by XRPD.

Example 10

Crystallization of Compound 1 Form A by Method H 20.5 mg of amorphous Compound 1 was added to a 2.5 mL stainless steel RETSCH® grinding container. Subsequently, 10 µL of isopropanol was added, along with 2 stainless steel balls (2 mm diameter). The container was sealed and mounted in a RETSCH® MM301 ball mill and the material was ground at a frequency of 30 Hz at close to ambient conditions (temperature of 23° C. and pressure ~100,000 Pa), for one hour. The steel balls were removed and material collected and analyzed by XRPD.

Example 11

Crystallization of Compound 1 Form B by Method I

Amorphous Compound 1 (19.7 mg) was suspended in 100 µL water in 1.8 mL vial. The obtained slurry was stirred at ambient conditions (temperature of 23° C. and pressure ~100,000 Pa) for 14 days. During the entire experiment, the solution was stirred at 30 rpm, using magnetic stirrer, and a TEFLON®-coated magnetic stirring bar with dimensions 7 mm in length and 2 mm in width. Upon completion, the mixture was centrifuged (speed: 3000 rpm, time: 10 min) and the liquid was removed using Pasteur pipette. The remaining wet solids were dried under air, at ambient conditions, for one hour before being analyzed by XRPD.

Example 12

Crystallization of Compound 1 Form B by Method D

A solution of about 100 mg/mL of Compound 1 was prepared using 40.4 mg of amorphous Compound 1 (amorphous) and 200 µL of a water/tetrahydrofuran (50/50 (v/v)) solvent mixture, at ambient temperature, in a 1.8 mL vial. The solution was heated to 60° C., with a heating rate of 10° C./min, and stirred at 30 rpm, using a TEFLON®-coated magnetic stirring bar with dimensions 7 mm in length and 2 mm in width, and subsequently passed through a preheated 0.45 µm PTFE filter to provide a clear solution. The solution was kept at 60° C. for one hour and then subjected to a cooling profile of cooling to 5° C. with a cooling rate of 1° C./hour. Solution was constantly stirred, as above. Solution was kept at 5° C. for 48 hours and then precipitated solid was collected by centrifugation (3000 rpm for 10 minutes) followed by solvent removal by Pasteur pipette. Solids were dried under ambient conditions and analyzed by XRPD.

Example 13

Preparation of Compound 1 Form A for FT-IR and Raman spectroscopy

Compound 1 Form A was generated through a modified Method C procedure, followed by a modified Method D procedure. To a solution of methanol (45.7 g; 58.1 mL; 1:0.79 w/w) and Compound 1 (57.9 g; 0.15 mmol; 1:1 w/w) in a round bottom flask at 25-30° C. was added tert-butyl methyl ether (171.2 g; 231.0 mL; 1:2.96 w/w) dropwise over a period of 45 minutes at 25-30° C. The reaction mass was slowly cooled to 8±2° C. and stirred at the same temperature for 45 minutes. After 45 minutes, the reaction mass was filtered and the cake washed with chilled tert-butyl methyl ether (85.6 g; 115.5 mL; 1:1.48 w/w). The product was dried under vacuum at 25±5° C. to afford 55.0 g of the purified Compound 1 Form A material (HPLC purity of 99.8 area %) which was used for FT-IR and Raman shift spectroscopy.

Example 14

FT-IR Spectroscopy Experimental Conditions

Compound 1 Form A material from Example 13 was used for FT-IR analysis.

FT-IR analysis was performed using a Thermo Nicolet Avatar 370 FT-IR instrument and FT-IR spectra were presented using GRAMS/AI spectroscopy software version 8.00. Instrument parameters were as follows: Number of scans=16, Number of background scans=16, Resolution=2.000, Sample gain=8.0, Mirror velocity=0.6329 and Aperture=100.00. Air background spectra were collected before the sample analysis. Representative FT-IR spectroscopy data for Compound 1 Form A, from Example 14 can be found in FIG. 8 and are indicative of FT-IR spectroscopy data generated from material for Compound 1 Form A performed by alternative crystallization methods.

Example 15

Raman Shift Spectroscopy Experimental Conditions

Compound 1 Form A material from Example 13 was used for Raman shift analysis.

Raman spectroscopy analysis was performed using a Raman station Avalon Instruments, software version 5.4.3.4 with cyclohexane used as a standard solvent for calibration and as reference spectrum for peak picking. The sample of powder was placed on a clean glass slide and placed directly below the laser pathway. Spectral data was collected using an exposure of 5 s×5 exposures to ensure powder was homogeneous and the collected spectra represented the bulk material. Representative raman shift spectroscopy data for Compound 1 Form A, from Example 15 can be found in FIG. 9 and are indicative of raman shift spectroscopy data generated from material for Compound 1 Form A performed by alternative crystallization methods.

All of the U.S. patents, U.S. patent application publications, U.S. patent applications, foreign patents, foreign patent applications and non-patent publications, including U.S. provisional patent application Ser. No. 62/185,416, filed Jun. 26, 2015, referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A crystalline form of the acetate salt of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol, designated as Compound 1 Form B, characterized by an X-ray powder diffraction pattern containing the following peaks: 5.5, 9.4 and 12.2 degrees 2Θ±0.3 degrees 2Θ.

2. The crystalline form of claim 1 further characterized by an X-ray powder diffraction pattern containing one or more of the following additional peaks: 9.0, 12.2, 12.9, 13.2, 14.0, 14.3, 15.4, 16.1, 16.6, 17.0, 18.0, 18.3, 19.0, 20.0, 21.3, 22.8, 24.4, 25.0, 25.8, 26.8, 27.3, 28.1, 28.9, 31.1, 32.5, 33.5, 34.3 and 36.3 degrees 2Θ±0.3 degrees 2Θ.

3. The crystalline form of claim 1 characterized by a DSC with an endothermic event with an onset at 170.4° C.±0.3° C. and a characterizing endothermic peak at 186.6° C.±0.3° C.

4. The crystalline form of claim 1 characterized by one or more of:
   XRPD pattern substantially set out in Table 5 and/or FIG. 10;
   DSC thermogram substantially set out in FIG. 11; and
   TGA thermogram substantially set out in FIG. 12.

5. A method for preparing the crystalline form of claim 1 comprising the steps of mixing the amorphous form of the acetate salt of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol with solvents of mixtures thereof selected from the group consisting of water and tetrahydrofuran.

* * * * *